(12) United States Patent
Korpman et al.

(10) Patent No.: US 10,878,955 B2
(45) Date of Patent: *Dec. 29, 2020

(54) INDIVIDUAL HEALTH RECORD SYSTEM AND APPARATUS

(71) Applicant: CENTRIFYHEALTH, LLC, Nashville, TN (US)

(72) Inventors: Ralph A. Korpman, Nashville, TN (US); Cindy A. Post, Colton, CA (US); Rudy R. Hilado, Leesburg, VA (US); W. Randal Clegg, Yucaipa, CA (US)

(73) Assignee: CENTRIFYHEALTH, LLC, Nashville, TN (US)

( * ) Notice: Subject to any disclaimer, the term of this patent is extended or adjusted under 35 U.S.C. 154(b) by 218 days.

This patent is subject to a terminal disclaimer.

(21) Appl. No.: 16/155,051

(22) Filed: Oct. 9, 2018

(65) Prior Publication Data

US 2019/0043614 A1 Feb. 7, 2019

Related U.S. Application Data

(63) Continuation of application No. 11/862,192, filed on Sep. 26, 2007, now Pat. No. 10,127,620.

(Continued)

(51) Int. Cl.
*G16H 40/20* (2018.01)
*G06Q 50/24* (2012.01)
(Continued)

(52) U.S. Cl.
CPC ............. *G16H 40/20* (2018.01); *G06Q 50/24* (2013.01); *G16H 10/60* (2018.01); *G16H 50/20* (2018.01)

(58) Field of Classification Search
USPC ........................................................ 705/2–4
See application file for complete search history.

(56) References Cited

U.S. PATENT DOCUMENTS 5,701,400 A 12/1997 Amado
5,724,575 A 3/1998 Hoover et al.
(Continued)

FOREIGN PATENT DOCUMENTS

CN 108564682 A 9/2018
EP 1145179 A2 10/2001
(Continued)

OTHER PUBLICATIONS

Schadow, Gunther, Daniel C. Russler, and Clement J. McDonald. "Conceptual alignment of electronic health record data with guideline and workflow knowledge." International journal of medical informatics 64.2-3 (2001): 259-274.*

(Continued)

*Primary Examiner* — Mark Holcomb
(74) *Attorney, Agent, or Firm* — Alston & Bird LLP

(57) ABSTRACT

A system, apparatus, and related methods for the collection, processing, evaluation, transformation, and reporting of individual health care information from diverse information systems and sources. A individual health record (IHR) of the present invention provides a structure for individuals to participate in, and manage, their health and their medical care, while still meeting the needs of health care organizations and caregivers. An IHR object may be formed by obtaining information from diverse health care information systems and sources, and transforming and re-purposing into a coherent account of the individual's overall health and care using a comprehensive health care ontology. As information from various sources is updated or available, the IHR is dynamically updated on a continuous or periodic basis. In one embodiment, the IHR system is contained in a self-contained package or "appliance" designed to "plug and play" in existing health care information technology systems and networks, with minimal effort and intervention.

21 Claims, 22 Drawing Sheets

Related U.S. Application Data

(60) Provisional application No. 60/826,967, filed on Sep. 26, 2006.

(51) Int. Cl.
    *G16H 10/60*     (2018.01)
    *G16H 50/20*     (2018.01)

(56) References Cited

U.S. PATENT DOCUMENTS

| | | |
|---|---|---|
| 5,937,409 A | 8/1999 | Wetherbee |
| 5,956,728 A | 9/1999 | Federighi et al. |
| 6,104,963 A | 8/2000 | Cebasek et al. |
| 6,163,781 A * | 12/2000 | Wess, Jr. ............... G06Q 40/08 |
| 6,272,468 B1 | 8/2001 | Melrose |
| 6,314,556 B1 * | 11/2001 | DeBusk ............... G06F 19/325 717/107 |
| 6,502,103 B1 | 12/2002 | Frey et al. |
| 6,519,605 B1 | 2/2003 | Gilgen et al. |
| 6,533,724 B2 | 3/2003 | McNair |
| 6,990,513 B2 | 1/2006 | Belfiore et al. |
| 7,349,859 B1 | 3/2008 | Lamer et al. |
| 7,533,030 B2 | 5/2009 | Hasan et al. |
| 7,720,691 B2 | 5/2010 | Hasan et al. |
| 8,090,590 B2 | 1/2012 | Fotsch et al. |
| 8,108,767 B2 | 1/2012 | Gaurav et al. |
| 8,307,338 B2 | 11/2012 | Ocke et al. |
| 8,412,541 B2 | 4/2013 | Qian et al. |
| 8,429,179 B1 | 4/2013 | Mirhaji |
| 8,478,766 B1 | 7/2013 | Tsypliaev et al. |
| 8,666,922 B2 | 3/2014 | Hohimer et al. |
| 8,756,191 B2 | 6/2014 | B'Far et al. |
| 9,754,220 B1 | 9/2017 | Brestoff et al. |
| 9,906,532 B2 | 2/2018 | Perez et al. |
| 9,973,455 B1 | 5/2018 | Fowler et al. |
| 2001/0051881 A1 * | 12/2001 | Filler ............... G16H 10/60 705/3 |
| 2002/0095482 A1 | 7/2002 | Shuster |
| 2002/0103811 A1 | 8/2002 | Fankhauser et al. |
| 2002/0138351 A1 | 9/2002 | Houvener et al. |
| 2002/0194221 A1 | 12/2002 | Strong et al. |
| 2003/0055679 A1 | 3/2003 | Soll et al. |
| 2003/0078813 A1 | 4/2003 | Haskell et al. |
| 2003/0172368 A1 | 9/2003 | Alumbaugh et al. |
| 2004/0019502 A1 | 1/2004 | Leaman et al. |
| 2004/0078217 A1 * | 4/2004 | Bacevice ............... G06Q 50/22 705/2 |
| 2004/0122706 A1 | 6/2004 | Walker et al. |
| 2004/0172307 A1 | 9/2004 | Gruber |
| 2004/0225629 A1 | 11/2004 | Eder |
| 2004/0249672 A1 | 12/2004 | Bocionek et al. |
| 2005/0055321 A1 | 3/2005 | Fratkina et al. |
| 2005/0158767 A1 | 7/2005 | Haskell et al. |
| 2005/0182661 A1 | 8/2005 | Allard et al. |
| 2005/0203771 A1 | 9/2005 | Achan |
| 2005/0228808 A1 | 10/2005 | Mamou et al. |
| 2005/0236474 A1 | 10/2005 | Onuma et al. |
| 2005/0273367 A1 | 12/2005 | Nourie et al. |
| 2005/0283382 A1 | 12/2005 | Donoghue et al. |
| 2006/0010011 A1 * | 1/2006 | Ullom ............... G06Q 50/22 705/2 |
| 2006/0020466 A1 | 1/2006 | Cousineau et al. |
| 2006/0020493 A1 | 1/2006 | Cousineau et al. |
| 2006/0052945 A1 | 3/2006 | Rabinowitz et al. |
| 2006/0080312 A1 | 4/2006 | Friedlander et al. |
| 2006/0112029 A1 | 5/2006 | Estes |
| 2006/0149573 A1 * | 7/2006 | Hoffman ............... G06Q 10/067 702/19 |
| 2006/0184389 A1 | 8/2006 | Benja-Athon et al. |
| 2006/0277215 A1 | 12/2006 | Siegel |
| 2007/0005621 A1 | 1/2007 | Lesh et al. |
| 2007/0006322 A1 | 1/2007 | Karimzadeh et al. |
| 2007/0016450 A1 | 1/2007 | Bhora et al. |
| 2007/0078677 A1 | 4/2007 | Hofstetter |
| 2007/0083607 A1 | 4/2007 | Thompson et al. |
| 2007/0106753 A1 | 5/2007 | Moore |
| 2007/0112714 A1 | 5/2007 | Fairweather |
| 2007/0118399 A1 | 5/2007 | Avinash et al. |
| 2007/0192137 A1 | 8/2007 | Ombrellaro |
| 2007/0203750 A1 | 8/2007 | Volcheck |
| 2007/0250405 A1 | 10/2007 | Ronen et al. |
| 2008/0040151 A1 | 2/2008 | Moore |
| 2008/0046292 A1 | 2/2008 | Myers et al. |
| 2008/0134133 A1 | 6/2008 | Dellostritto et al. |
| 2009/0070148 A1 | 3/2009 | Skocic |
| 2010/0036680 A1 | 2/2010 | Familant |
| 2011/0119291 A1 | 5/2011 | Rice |
| 2011/0225176 A1 | 9/2011 | Siegel et al. |
| 2011/0246230 A1 | 10/2011 | Sie et al. |
| 2012/0215560 A1 | 8/2012 | Ofek et al. |
| 2013/0262474 A1 | 10/2013 | Curran et al. |
| 2013/0311419 A1 | 11/2013 | Xing et al. |
| 2013/0346103 A1 | 12/2013 | Griffin et al. |
| 2016/0085914 A1 | 3/2016 | Douglass et al. |
| 2016/0110525 A1 | 4/2016 | Power et al. |
| 2016/0132645 A1 | 5/2016 | Charpentier et al. |
| 2016/0267222 A1 | 9/2016 | Larcom et al. |
| 2016/0267484 A1 | 9/2016 | Smoley et al. |
| 2017/0046425 A1 | 2/2017 | Tonkin et al. |
| 2017/0169339 A1 | 6/2017 | Dalmia et al. |
| 2018/0060503 A1 | 3/2018 | Allen |
| 2018/0089383 A1 | 3/2018 | Allen et al. |
| 2018/0210925 A1 | 7/2018 | Raghavan et al. |
| 2018/0211058 A1 | 7/2018 | Aunger et al. |
| 2018/0300310 A1 | 10/2018 | Shinn et al. |
| 2018/0300640 A1 | 10/2018 | Birnbaum et al. |
| 2018/0358112 A1 | 12/2018 | Sharifi Sedeh et al. |
| 2019/0005012 A1 | 1/2019 | Priestas et al. |
| 2019/0005019 A1 | 1/2019 | Burke et al. |
| 2019/0051416 A1 | 2/2019 | Monteverde |

FOREIGN PATENT DOCUMENTS

| | | |
|---|---|---|
| EP | 2019362 A2 | 1/2009 |
| EP | 2302533 A1 | 3/2011 |
| JP | 2005-135207 A | 5/2005 |
| WO | 2000/057339 A2 | 9/2000 |
| WO | 2002/031738 A1 | 4/2002 |
| WO | 2014/089063 A1 | 6/2014 |

OTHER PUBLICATIONS

U.S. Patent and Trademark Office, Notice of Allowance for U.S. Appl. No. 14/308,873, dated Aug. 23, 2019, (19 pages), USA.

Webster A Methodology for incorporating web technologies into a computer-baesd patient record, Int'l J Medical Informatics, vol. 68, Issues 1-3, Dec. 2002, pp. 39-47; available at https://doi.org/10.1016/S1386 5056(02)00062-X.

Supplementary European search report dated Oct. 1, 2012 for EP Application No. 07853641.

Perez-Rey, D. et al. "Ontofusion: Ontology-based Integration of Genomic and Clinical Databases", Jul. 1, 2006, Computers in Biology and Medicine, pp. 712-730, vol. 36, No. 7-8.

Paterson, G. I. (2007). Boundary infostructures for chronic disease. (Order No. NR27167, Dalhousie University (Canada)). ProQuest Dissertations and Theses, , 183-n/a. Retrieved from http://search.proquest.com/docview/304792954?accountid=14753. (304792954).

Outgoing Written Opinion of the ISA dated Mar. 13, 2008 for WO Application No. PCT/US07/079609.

Outgoing—ISA/210—International Search Report dated Mar. 13, 2008 for WO Application No. PCT/US07/079609.

Notice of Allowance and Fees Due (PTOL-85) dated Sep. 12, 2018 for U.S. Appl. No. 11/862,192.

Notice of Allowance and Fees Due (PTOL-85) dated Jul. 11, 2018 for U.S. Appl. No. 11/862,192.

Notice of Allowance and Fees Due (PTOL-85) dated Aug. 28, 2013 for U.S. Appl. No. 12/723,753.

Non-Final Rejection dated Oct. 12, 2011 for U.S. Appl. No. 12/723,753.

(56) References Cited

OTHER PUBLICATIONS

Non-Final Rejection dated Nov. 28, 2016 for U.S. Appl. No. 14/937,354.
Non-Final Rejection dated Nov. 12, 2014 for U.S. Appl. No. 11/862,192.
Non-Final Rejection dated May 20, 2015 for U.S. Appl. No. 14/308,873.
Non-Final Rejection dated Jan. 28, 2015 for U.S. Appl. No. 14/041,769.
Non-Final Rejection dated Jan. 10, 2018 for U.S. Appl. No. 14/937,354.
Non-Final Rejection dated Feb. 7, 2017 for U.S. Appl. No. 14/308,873.
Non-Final Rejection dated Aug. 10, 2010 for U.S. Appl. No. 11/862,192.
Non-Final Rejection dated Aug. 1, 2017 for U.S. Appl. No. 11/862,192.
Non-Final Rejection dated Apr. 27, 2018 for U.S. Appl. No. 14/792,330.
Non-Final Rejection dated Apr. 23, 2013 for U.S. Appl. No. 12/723,753.
Non-Final Rejection dated Apr. 22, 2013 for U.S. Appl. No. 11/862,192.
Non-Final Rejection dated Apr. 5, 2016 for U.S. Appl. No. 11/862,192.
Kerkri, E. M. et al. "An Approach for Integrating Heterogeneous Information Sources in a Medical Data Warehouse", Jan. 1, 2001, Journal of Medical Systems, pp. 167-176, vol. 25, No. 3.
ISA/220—Notification of Transmittal or Search Report and Written Opinion of the ISA, or the Declaration dated Mar. 13, 2008 for WO Application No. PCT/US07/079609.
International Search Report and Written Opinion of the International Searching Authority, PCT/US07/79609 (filed Sep. 26, 2007).
Final Rejection dated Oct. 9, 2015 for U.S. Appl. No. 14/041,769.
Final Rejection dated Nov. 28, 2017 for U.S. Appl. No. 11/862,192.
Final Rejection dated Nov. 23, 2016 for U.S. Appl. No. 11/862,192.
Final Rejection dated Jun. 7, 2012 for U.S. Appl. No. 12/723,753.
Final Rejection dated Jun. 4, 2015 for U.S. Appl. No. 11/862,192.
Final Rejection dated Feb. 4, 2011 for U.S. Appl. No. 11/862,192.
Final Rejection dated Feb. 1, 2016 for U.S. Appl. No. 14/308,873.
Final Rejection dated Dec. 6, 2013 for U.S. Appl. No. 11/862,192.
Final Rejection dated Aug. 25, 2017 for U.S. Appl. No. 14/937,354.
Final Rejection dated Aug. 22, 2017 for U.S. Appl. No. 14/308,873.
European search report dated Apr. 19, 2017 for EP Application No. 16178790.
European search opinion dated Oct. 1, 2012 for EP Application No. 07853641.
European search opinion dated Apr. 19, 2017 for EP Application No. 16178790.
Communication from the Examining Division dated Jan. 8, 2014 for EP Application No. 07853641.
Chong, Q. et al., "Ontology Based Metadata Management in Medical Domains", May 1, 2003, Journal of Research and Practice in Information Technology, pp. 139-153, vol. 35, No. 2.
Applicant Initiated Interview Summary (PTOL-413) dated Oct 17, 2017 for U.S. Appl. No. 14/308,873.
Applicant Initiated Interview Summary (PTOL-413) dated Jul. 2, 2013 for U.S. Appl. No. 12/723,753.
Applicant Initiated Interview Summary (PTOL-413) dated Apr. 4, 2013 for U.S. Appl. No. 12/723,753.
Annex to the communication dated Jul. 7, 2016 for EP Application No. 07853641.
Annex to the communication dated Jan. 8, 2014 for EP Application No. 07853641.
Annex to the communication dated Jan. 5, 2016 for EP Application No. 07853641.
Annex to the communication dated Aug. 4, 2016 for EP Application No. 07853641.
Armstrong, Eric, "Working With XML—The Java API for XML Parsing (JAXP) Tutorial," Version 1.1, Update 31, Aug. 21, 2001 (494 pages).
International Searching Authority, International Search Report and Written Opinion for International Application No. PCT/US2020/025642, dated Jul. 2, 2020, (14 pages), Rijswijk, Netherlands.
International Searching Authority, International Search Report and Written Opinion for International Application No. PCT/US2020/025653, dated Jul. 2, 2020, (14 pages), Rijswijk, Netherlands.
International Searching Authority, International Search Report and Written Opinion for International Application No. PCT/US2020/025668, dated Jul. 1, 2020, (14 pages), Rijswijk, Netherlands.
International Searching Authority, International Search Report and Written Opinion for International Application No. PCT/US2020/025721, dated Jul. 2, 2020, (10 pages), Rijswijk, Netherlands.
International Searching Authority, International Search Report and Written Opinion for International Application No. PCT/US2020/025764, dated Jul. 2, 2020, (10 pages), Rijswijk, Netherlands.
International Searching Authority, International Search Report and Written Opinion for International Application No. PCT/US2020/025788, dated Jul. 2, 2020, (14 pages), Rijswijk, Netherlands.
International Searching Authority, International Search Report and Written Opinion for International Application No. PCT/US2020/025831, dated Jul. 2, 2020, (14 pages), Rijswijk, Netherlands.
International Searching Authority, International Search Report and Written Opinion for International Application No. PCT/US2020/025833, dated Jul. 2, 2020, (14 pages), Rijswijk, Netherlands.
United States Patent and Trademark Office, Final Office Action for U.S. Appl. No. 16/532,937, dated May 21, 2020, (29 pages), USA.
United States Patent and Trademark Office, NonFinal Office Action for U.S. Appl. No. 16/532,937, dated Nov. 21, 2019, (24 pages), USA.
Final Rejection dated Feb. 6, 2019 for U.S. Appl. No. 14/792,330.
United States Patent and Trademark Office. Final Office Action for U.S. Appl. No. 14/792,330, dated Apr. 16, 2020, (42 pages), USA.
U.S. Patent and Trademark Office, NonFinal Office Action for U.S. Appl. No. 14/792,330, dated Sep. 27, 2019, (22 pages), USA.
Summons to Attend Oral Proceedings Pursuant to Rule 115(1) EPC for European Patent Application No. 16178790.8, dated Apr. 24, 2020, (24 pages), European Patent Office, Munich, Germany.
International Preliminary Examining Authority, Second Written Opinion of the International Preliminary Examining Authority for International Application No. PCT/US2020/025642, dated Oct. 9, 2020, (8 pages), European Patent Office, Munich, Germany.
International Preliminary Examining Authority, Second Written Opinion of the International Preliminary Examining Authority for International Application No. PCT/US2020/025653, dated Oct. 8, 2020, (8 pages), European Patent Office, Munich, Germany.
International Preliminary Examining Authority, Second Written Opinion of the International Preliminary Examining Authority for International Application No. PCT/US2020/025668, dated Oct. 12, 2020, (8 pages), European Patent Office, Munich, Germany.
International Preliminary Examining Authority, Second Written Opinion of the International Preliminary Examining Authority for International Application No. PCT/US2020/025721, dated Oct. 8, 2020, (8 pages), European Patent Office, Munich, Germany.
International Preliminary Examining Authority, Second Written Opinion of the International Preliminary Examining Authority for International Application No. PCT/US2020/025764, dated Oct. 13, 2020, (8 pages), European Patent Office, Munich, Germany.
International Preliminary Examining Authority, Second Written Opinion of the International Preliminary Examining Authority for International Application No. PCT/US2020/025788, dated Oct. 13, 2020, (8 pages), European Patent Office, Munich, Germany.
International Preliminary Examining Authority, Second Written Opinion of the International Preliminary Examining Authority for International Application No. PCT/US2020/025831, dated Oct. 13, 2020, (9 pages), European Patent Office, Munich, Germany.
International Preliminary Examining Authority, Second Written Opinion of the International Preliminary Examining Authority, for International Application No. PCT/US2020/025833, dated Oct. 15, 2020, (8 pages), European Patent Office, Munich, Germany.
United States Patent and Trademark Office, NonFinal Office Action for U.S. Appl. No. 14/792,330, dated Oct. 2, 2020, (27 pages), USA.

\* cited by examiner

INDIVIDUAL HEALTH RECORD SYSTEM AND APPARATUS

CROSS-REFERENCE TO RELATED APPLICATIONS

The present application is a continuation of U.S. patent application Ser. No. 11/862,192 for filed Sep. 26, 2007, which claims the benefit of U.S. Provisional Application No. 60/826,967, filed Sep. 26, 2006, the entire contents of which are incorporated herein by reference.

BACKGROUND

Technical Field

This invention relates to a system, apparatus, and associated methods for the collection, processing, evaluation, transformation, and reporting of individual health care information from diverse information systems and sources.

Related Art

Most information technology (IT) applications are built on predefining, with great specificity, the types and construction of information to be received, sent, processed, and stored by the IT service or application. For many industries, this model works fairly well. In the health care industry, this model may work passably well when the application is used in operating a particular institution or practice where the relevant information is fairly limited, and can be specifically defined, collected, and managed. Even in such limited circumstances, however, such applications have problems because of the inherent randomness in biologic functions. This inherent unpredictability of biologic functions means that an individual's health does not follow a predefined course, making it a particularly difficult automation challenge.

This model does not work well for an individual-centric approach to health care. Health care is transforming from a traditional, provider-centric, organizational-driven approach to an individual-centered system. This individual-centered approach cuts across all providers and patients, and the interrelationships of sources of information cannot be predicted in advance. In addition, the information and relationships will vary widely from person to person, place to place, and time to time. Furthermore, because a broad range of patients, practitioners, and other health care stakeholders will be accessing and using the information for a variety of purposes, not only are the sources not predefined, but uses of the information are not predetermined either. Attempting to create a comprehensive, workable system for handling individual health care records using current models results in enormous, unwieldy databases and applications that are expensive and slow to operate and maintain, and prevent such systems from fulfilling their functions.

Accordingly, what is needed is a new model and approach to creating and maintaining individual health records that is robust and flexible enough to handle health information from a wide variety of unpredictable sources, and permits a broad range of patients, practitioners, and other users to manipulate and use health information in a wide variety of unpredictable ways.

BRIEF SUMMARY

The present invention is a system, apparatus, and related methods for the collection, processing, evaluation, transformation, and reporting of individual health care information from diverse information systems and sources. Health care is transforming from a traditional, provider-centric, organizational-driven approach to an individual-centered system. The individual health record (IHR) of the present invention provides a structure for individuals to participate in, and manage, their health and their medical care, while still meeting the needs of health care organizations and caregivers, thereby supporting collaborative care in a new way.

The IHR is formed by obtaining information from diverse health care information systems and sources, including, but not limited to, existing systems and information flows such as employee health records, pharmacies, laboratories, and medical claims information streams. The information from these sources is transformed and re-purposed into a coherent account of the individual's overall health and care. The IHR is not a 10 simple collection of all health care information about the individual; instead, the information is processed by means of an individual health information model that incorporates a comprehensive health care ontology.

In one exemplary embodiment, information is received from a source, validated, parsed, transformed, matched to an existing individual, and assigned an ontology concept code. Next, a message object is created, the data is repurposed, subjected to a rules evaluation, and filed in an IHR database. As information from various sources is updated or available, the IHR is dynamically updated on a continuous or periodic basis. A Single Best Record (SBR) of information may be created.

In other exemplary embodiments, the invention provides ways and means to 20 interact with the information in the IHR in a variety of ways, including through health portals, portlets, and web services. It allows individuals to understand and participate in their health care, and enables caregivers and consumers to collaborate and interact using the same record in different ways. It embraces the emerging roles of custodian and health care advocate, and assists health care stakeholders, including but not limited to health systems, health plans, IPAs, RHIOs, employers, providers, and individuals, to meet the requirements and needs for health care systems going forward into the future.

In one exemplary embodiment, the present invention does not replace existing information systems and infrastructure; instead, it provides a standards-based, service-oriented infrastructure that rapidly and easily provides health-related information and components that work with such existing systems.

In another exemplary embodiment, the IHR system is contained in a self-contained package or "appliance." The IHR appliance is designed to "plug and play" in existing health care information technology systems and networks, with minimal effort and intervention. Information is obtained from all available source systems and dynamically constructed into the IHR.

DETAILED DESCRIPTION OF THE VARIOUS EMBODIMENTS

Figure 1:
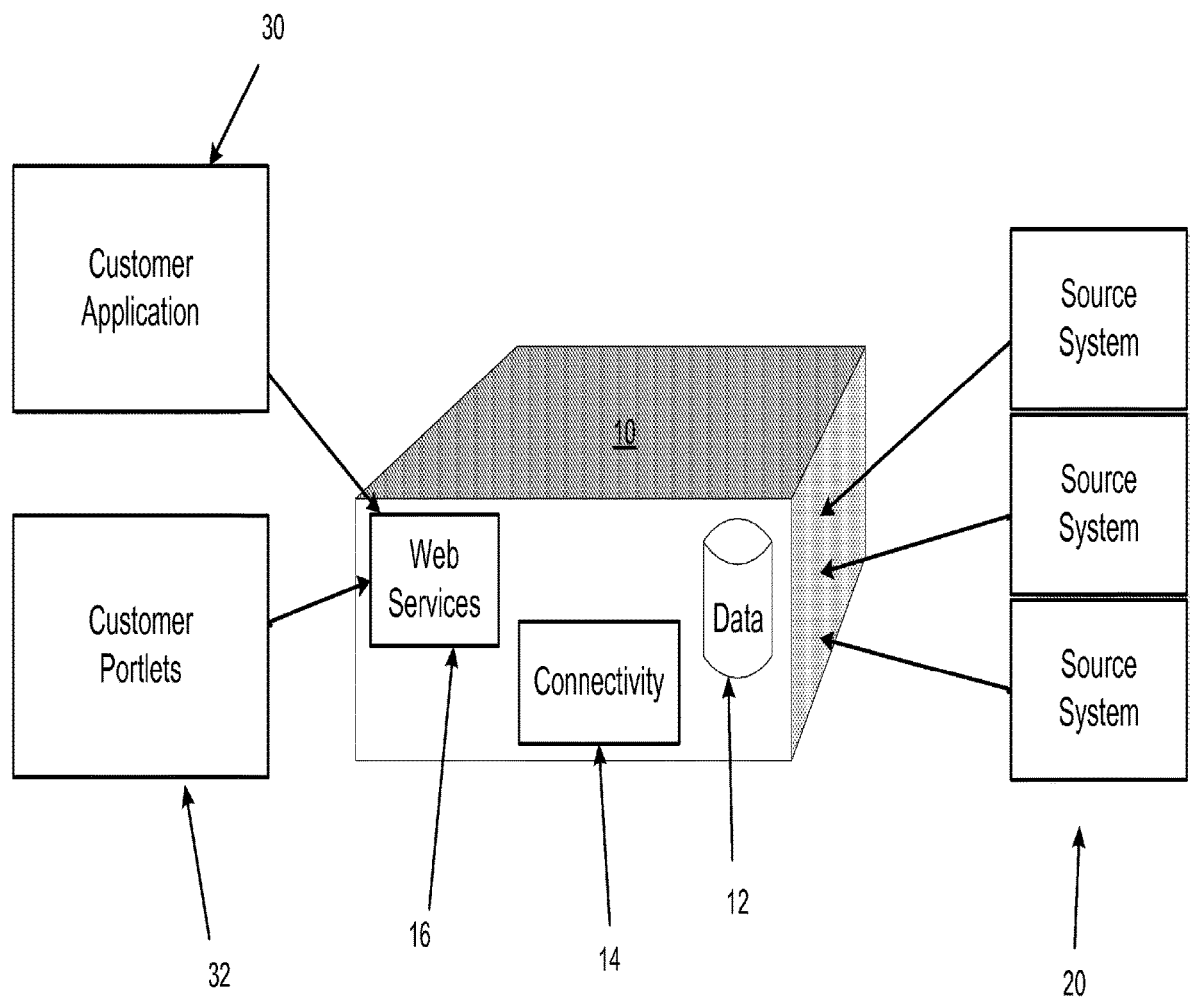
FIG. 1 is an overview of an IHR system in accordance with one embodiment of the present invention.

The present invention is a system, apparatus, and related methods for the collection, processing, evaluation, transformation, and reporting of individual health care information from diverse and potentially unpredictable information systems and sources, which also allows a wide variety of patients, health care givers, practitioners, and other users to manipulate and use the information in a variety of potentially unpredictable ways. The individual health record (IHR) system of the present invention provides a structure for individuals to participate in, and manage, their health and their medical care, while still meeting the needs of health care organizations and caregivers, thereby supporting collaborative health care in a new way.

The present invention uses a new business object model approach, known as Health Universal Genericity (HUG). This approach presumes that received information can be represented by a handful of highly abstracted health objects. These abstractions include, but are not limited to, health events, health conditions, health services, health products, and health relationships. Individual objects are created from data shared among these abstracted health objects through the unique interplay of "data objects," which exist only to hold data in support of the IHR-supported health delivery process. Each object's attributes are a composite of specific variables defined in the object class, extended by non-programmatically supported user-defined attributes.

In one exemplary embodiment, the IHR is formed by obtaining information from diverse health care information systems and sources, including, but not limited to, existing systems and information flows such as employee health records, pharmacies, laboratories, and medical claims information streams. The information from these sources is transformed and re-purposed into a coherent account of the individual's overall health and care. The IHR is not a simple collection of all health care information about the individual; instead, the information is processed by means of an individual health information model that incorporates a comprehensive health care ontology.

The system of the present invention has several unique characteristics that distinguish it from prior art systems. First, the level of abstraction is far higher than has been generally used in health care. High level abstract objects appropriate to each individual's health care are used, rather than the specific, detailed objects specific to each care setting used in the prior art. The use of these high level abstract objects in the present invention allows broad adaptability and flexibility without the intervention of programming modifications and resources that would required to effect changes in other systems. Second, the extension of the object model by binding it to the comprehensive health care ontology changes the meaning and use of the traditional object paradigm. Third, the system can take potentially all information about an individual (including, but not limited to, clinical, financial, personal, health, and administrative information), and represent it in a single, unified fashion. The system thereby can tie together not only the matching clinical-to-clinical or financial-to-financial transactions, but transactions or interactions across these traditionally separate data streams as well. This presents a uniquely robust view of each individual, his or her health care status, and the relationships of the health care system. Fourth, the system has the ability to extend the health objects, and their behavior, by modifying the ontology rather than the objects themselves. This modification can be done non-programmatically, thereby providing increased installability and flexibility over the prior art. Fifth, the creation of a health object from a metadata data object by the process of "centrification" (as discussed in more detail below) allows both preservation of the source information and simultaneous repurposing of the information to a uniform and unified representation. It should be noted that the system of the present invention does not use an XML-like approach, where data fields and their definitions are stored as pairs but the underlying infrastructure knows nothing about either part; in the case of the present invention the infrastructure is fully informed regarding both parts.

In one exemplary embodiment, the set of healthcare objects are unique, and allow virtually any health instance or activity to be characterized and interrelated to other health information known about, or to be known about, about an individual. Each object may comprise methods, attributes, and inheritances.

Figure 2:
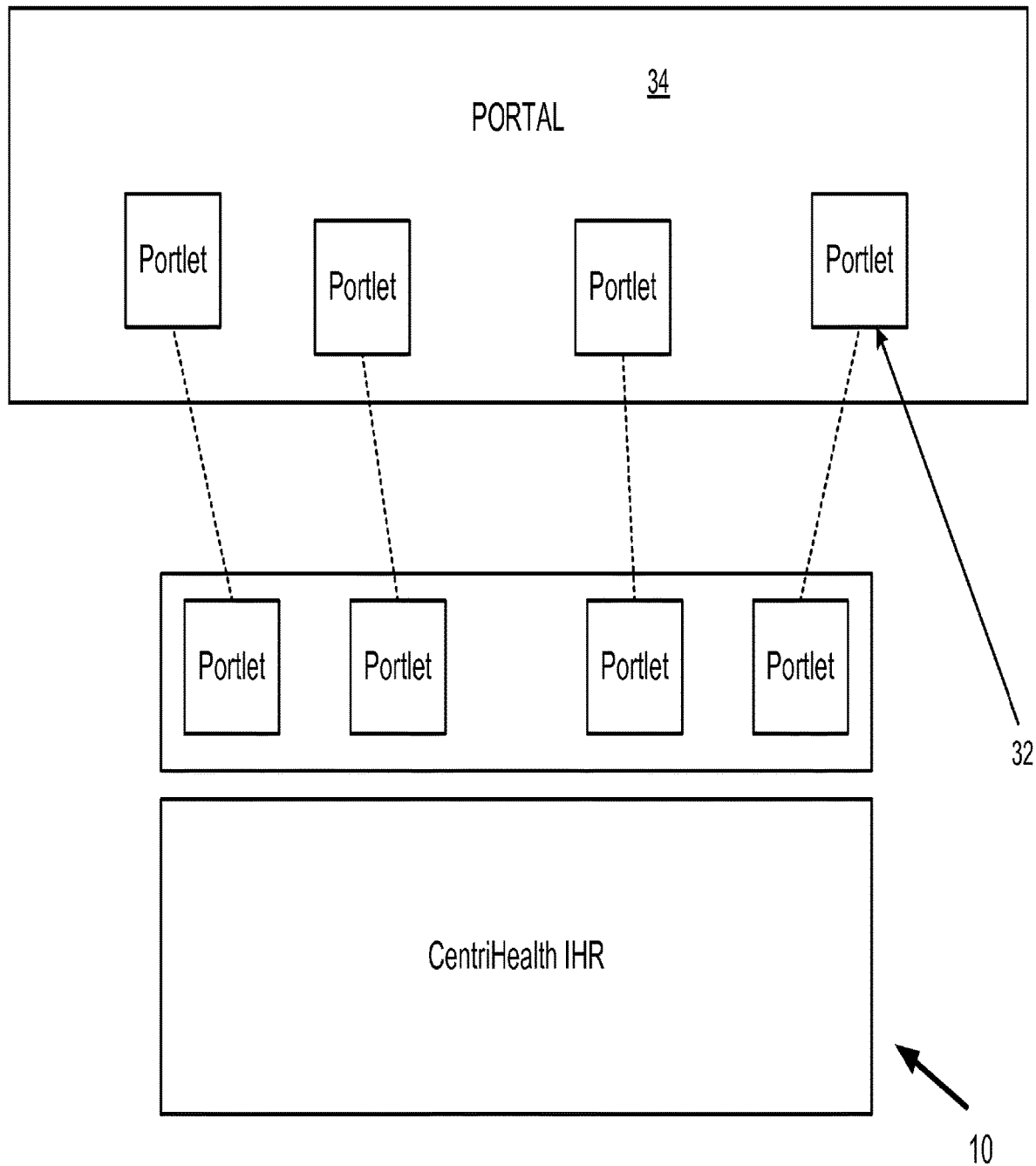
FIG. 2 is a diagram of customer portlets in a customer portal in accordance with an embodiment of the present invention.

FIG. 1 shows a broad, abstract view of an IHR system. The core IHR application 10 comprises the health data 12, connectivity services 14, and Internet Web services 16. Data is received from a variety of source systems 20. A variety of different types of users can access the IHR system through customer applications 30 or customer portlets 32 (described in more detail below). Customer portlets 32 may be used in customer portals 34, as shown in FIG. 2.

Figure 3:
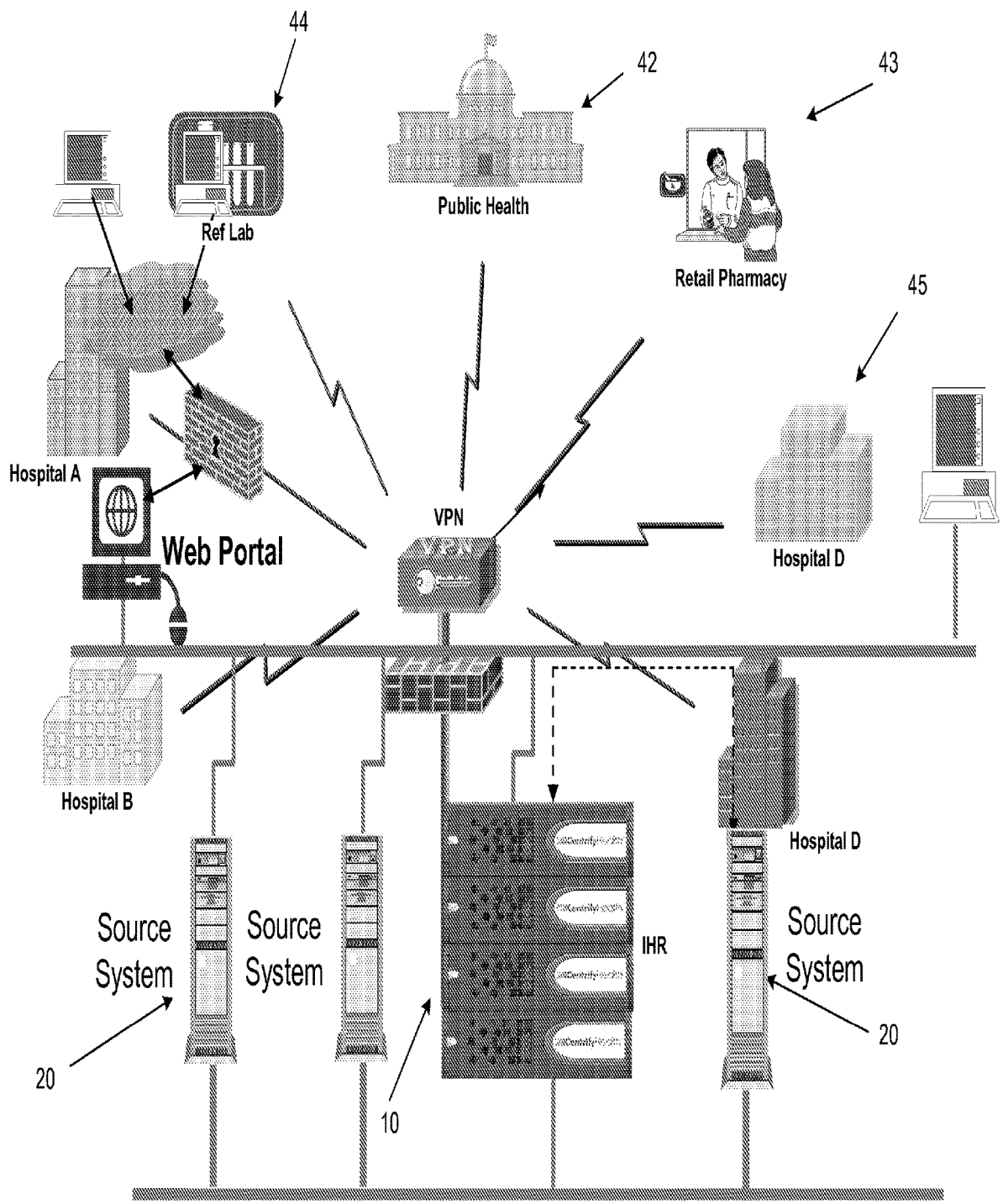
FIG. 3 is another view of an IHR system in accordance with one embodiment of the present invention.
Figure 17:
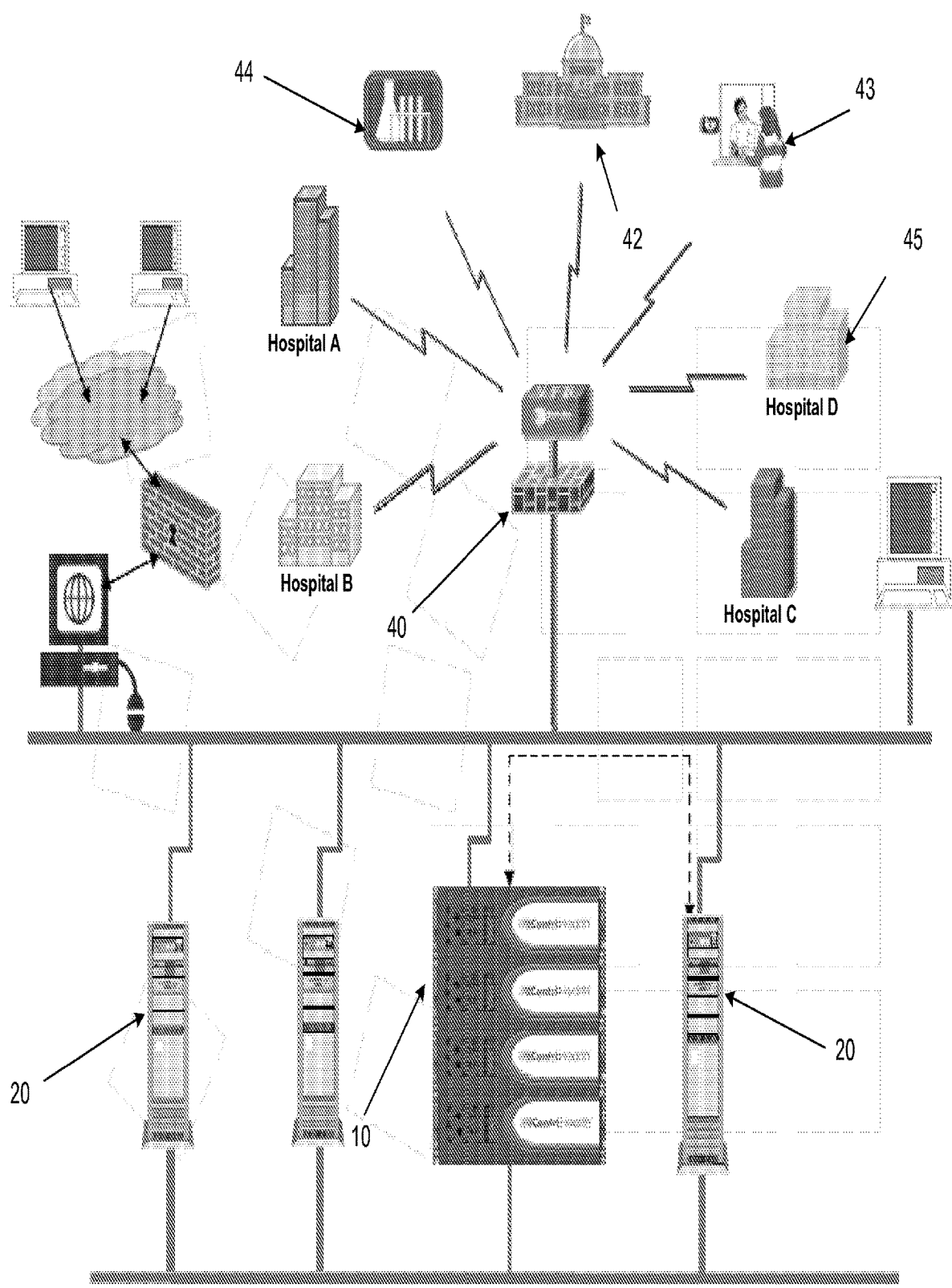
FIG. 17 is another view of an IHR system in accordance with one embodiment of the present invention.

FIGS. 3 and 17 show the IHR application 10 as an appliance installed in a customer's existing IT system behind a firewall 40. Information is received from a variety of source systems 20. Users include, but are not limited to, public health entities 42, retail pharmacies 43, labs 44, and hospitals 45.

Figure 4:
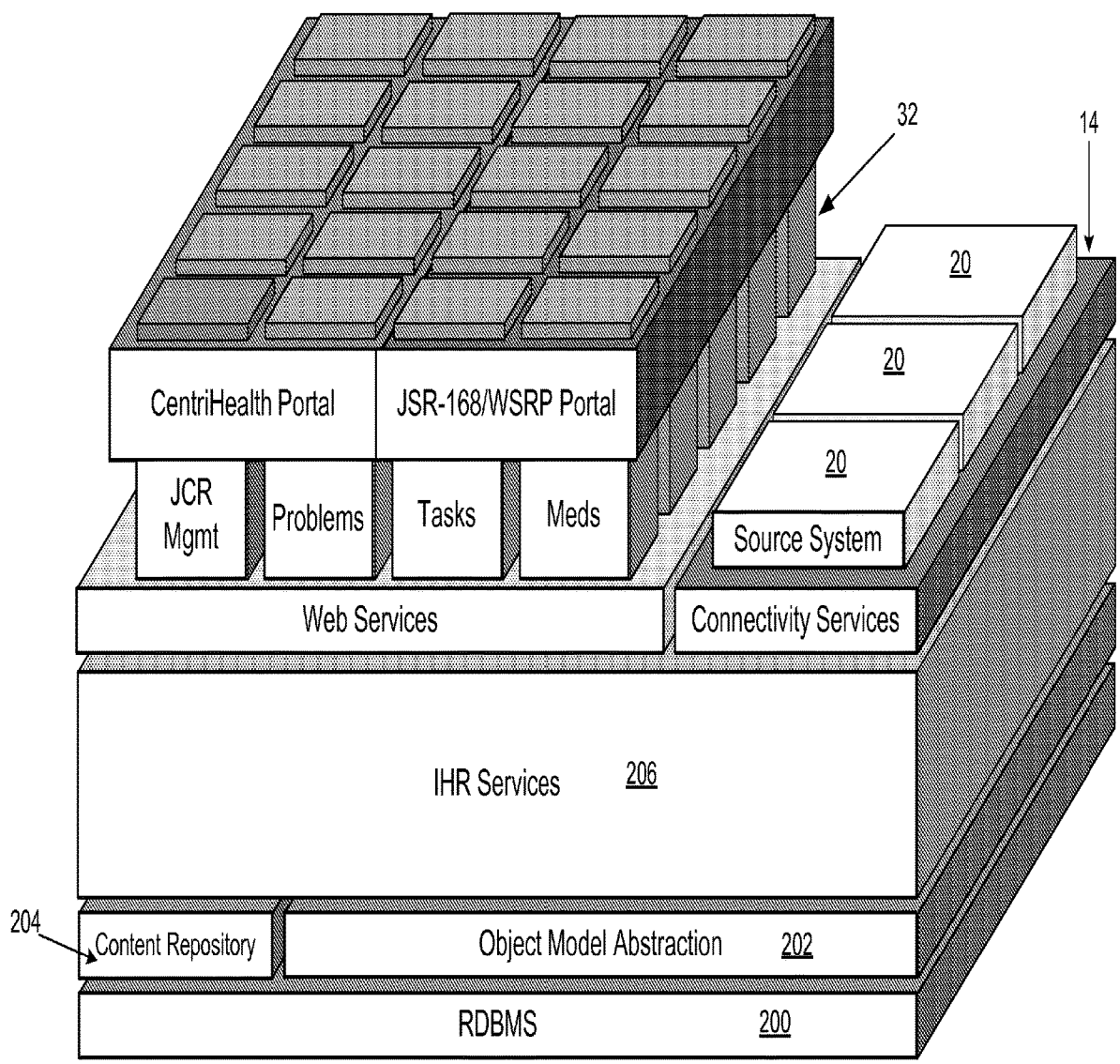
FIG. 4 is yet another view of an IHR system in accordance with one embodiment of the present invention.
Figure 18:
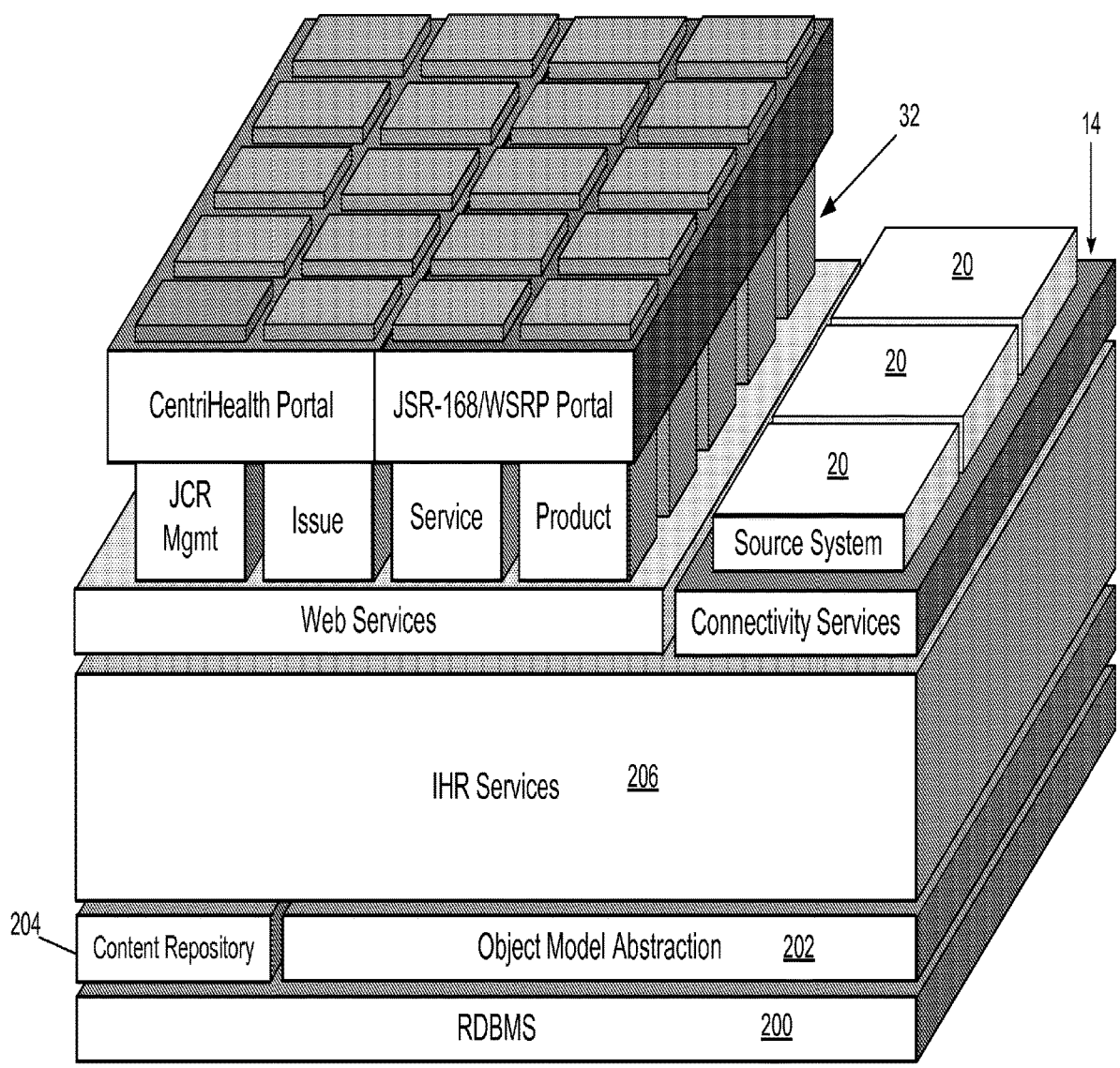
FIG. 18 is yet another view of an IHR system in accordance with one embodiment of the present invention.

In one exemplary embodiment, as shown in FIGS. 4 and 18, the IHR system comprises a persistent data storage layer 200, with a full object model 202 in the application layer supported by hibernate object and relational mapping. Part of the persistence layer comprises a content repository 204 provides a storage mechanism for IHR content items, such as binary large objects and other typically non-object oriented data (e.g., images, documents, rule definitions, message templates, information content, and help files), and may comprise standardized technology (e.g., Java). Content attributes or meta data associated with content items may be used for management and selection of discrete content items. Examples of attributes include, but are not limited to, ontology classes, target age, target gender, usage context, effective time, expiration time, keywords, status and location. The content repository may be viewed as a generic application data "super store," in which virtually any type of content can be handled, and that separates content from data storage technology. Content may be XML exportable and importable. A standard API (such as JSR 170 or JSR 238) may be used to interact with a content repository, thereby providing advantages such as the ability to access other standard content repositories, allow external editing, and transport content between Java content repositories.

Figure 5:
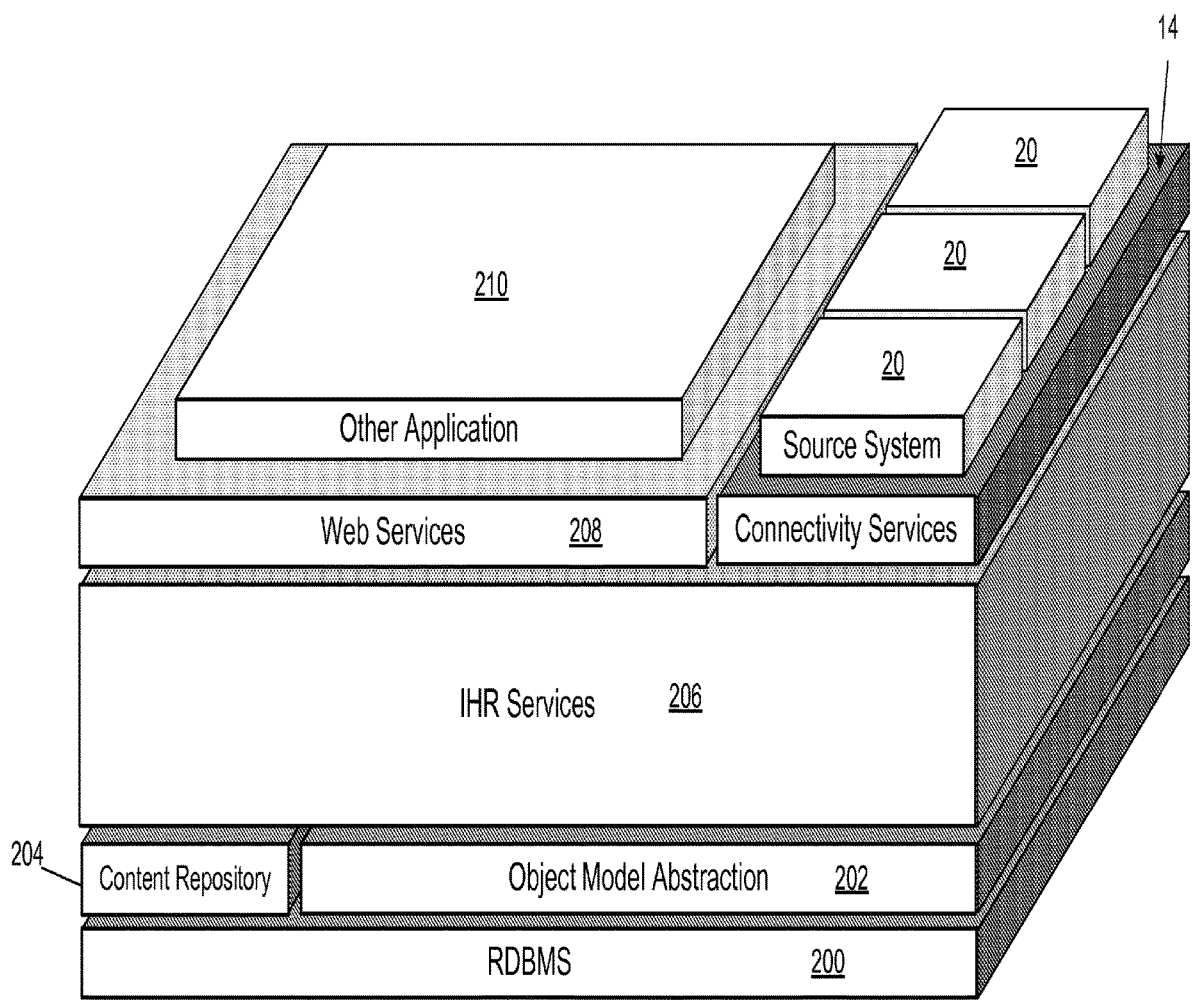
FIG. 5 is another view of an IHR system showing a customized application of an IHR system in accordance with one embodiment of the present invention.

The IHR Services layer 206 provides main IHR capabilities, including but not limited to centification services, interaction services, custodial services, and system administration services. Connectivity services 14 provide interface means with source systems 20, and handle messages and record parsing. Connection adapters may be used. The web services component 208 provides external access by users to the IHR data and functions through a variety of portlets 32, which may include customer written applications. In one exemplary embodiment, web applications may be instantiated as Java Specification Request 168 (JSR-168) or Web Services for Remote Portlets (WSRP) standard portlets. As seen in FIG. 5, other applications 210 can call web services 208 to create a customized solution.

Figure 6:
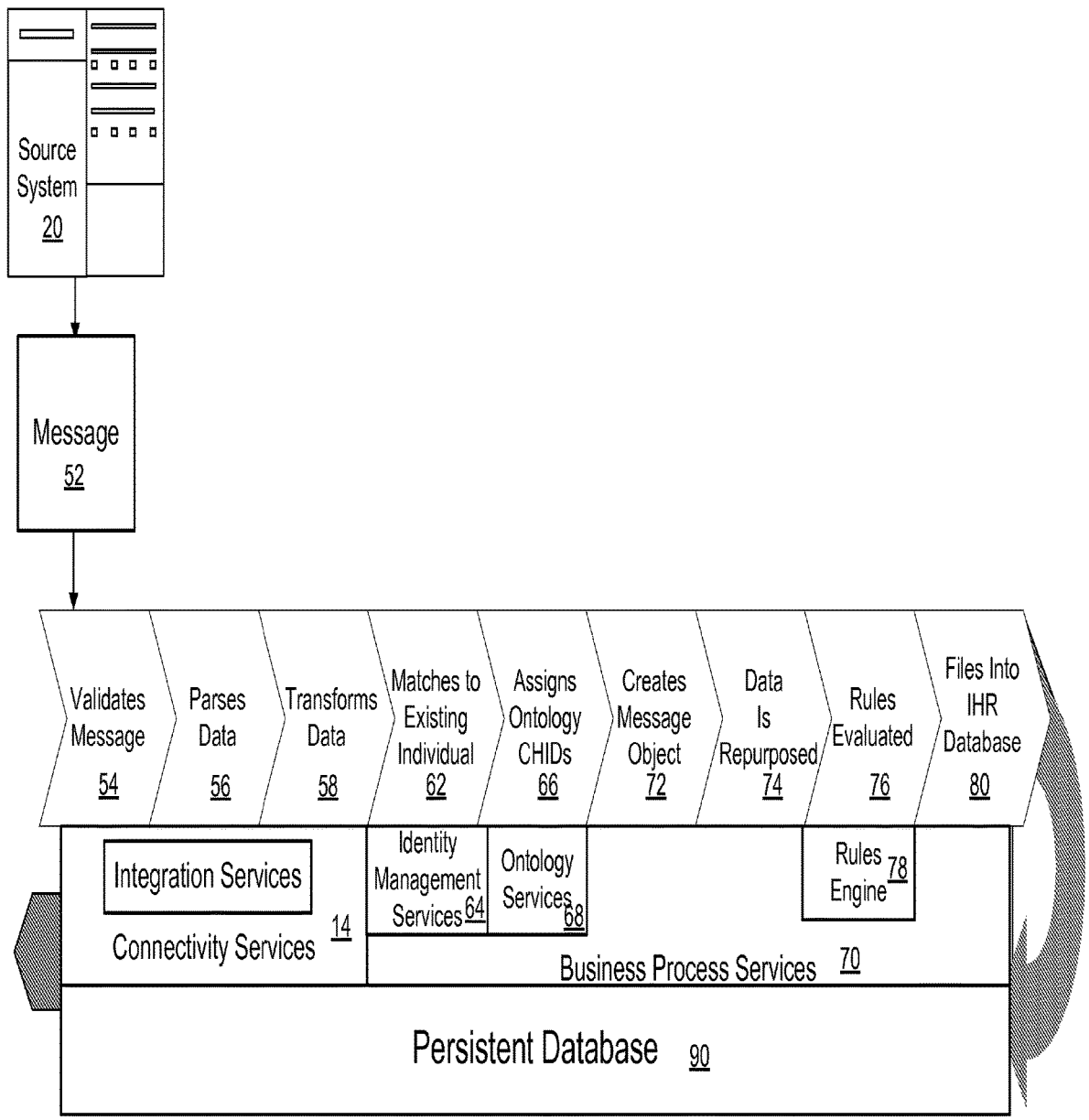
FIG. 6 is a diagram of data flows in accordance with one embodiment of the present invention.
Figure 19:
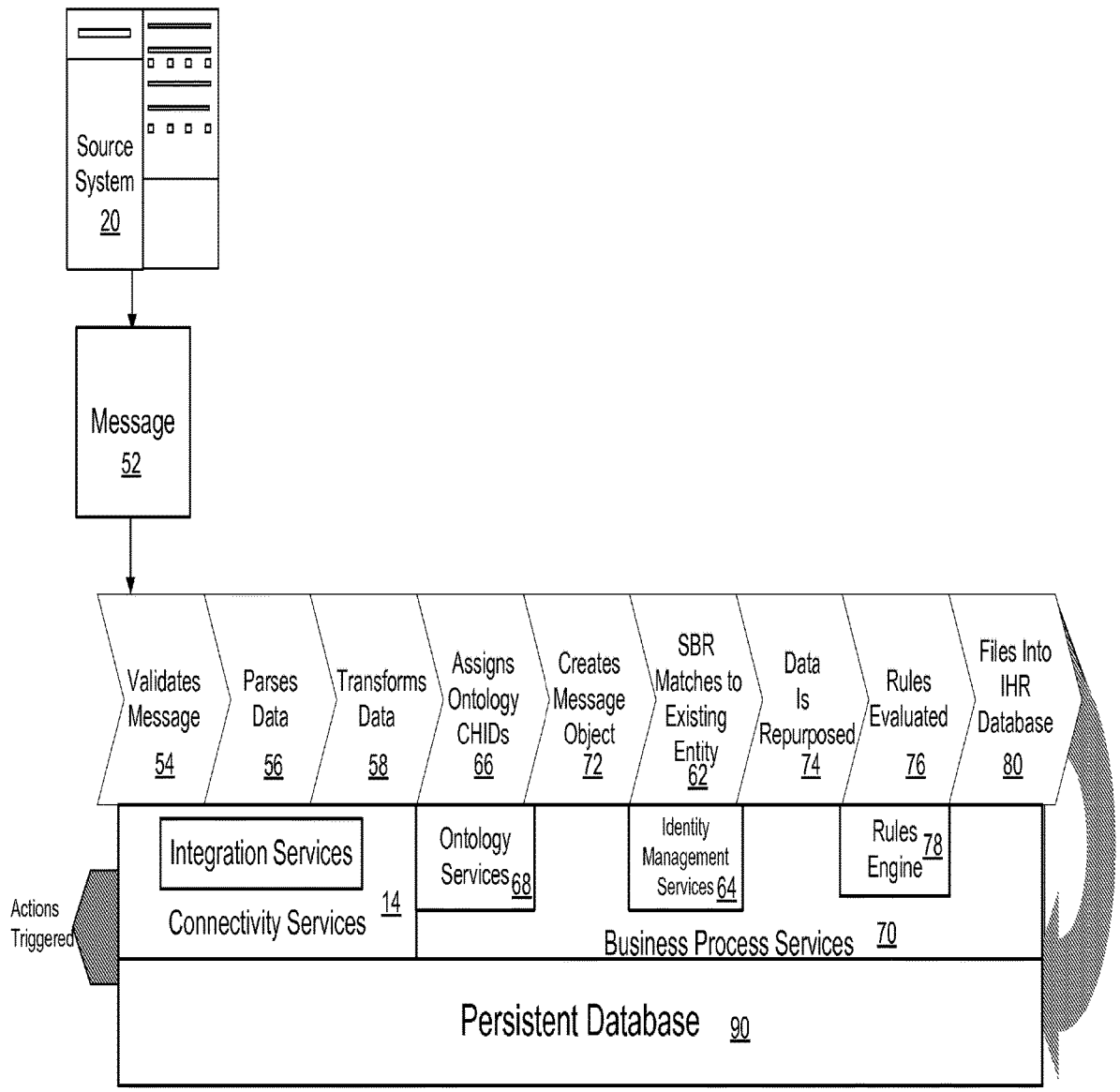
FIG. 19 is a diagram of data flows in accordance with one embodiment of the present invention.

FIGS. 6 and 19 show a general, broad overview of data flows in accordance with one embodiment of the subject invention. Information and data in the form of a "message" 52 (although some other form or terminology is possible) is received from a source 50, validated 54, parsed 56, and transformed 58. These steps are accomplished through integration services as part of the connectivity services 14. The transformed data is then matched 62 to an existing individual through identity management services 64, and assigned an ontology concept code 66 (CHID, discussed below) through ontology services 68. Next, a message object is created 72, the data is repurposed 74, subjected to a rules evaluation 76 using the rules engine 78, and filed 80 in a persistent IHR database 90. Some of these steps may be performed in another order, as shown in FIG. 19. The identity management services 64, ontology services 68, and rules engine 78 are components of the business process services 70 element of the IHR system. As information from various sources is updated or available, the IHR is dynamically updated on a continuous or periodic basis.

The connectivity services 14 component handles the connections with health data source systems. In one exemplary embodiment, the connectivity services uses an open-source cross-platform HL7 interface engine, although other platforms may be used. A connectivity configuration manager stores configuration data and manages the deployment environments. The platform monitors and manages the connectivity runtime components, including the connectivity designer used to define the specific message handling processes, connectivity adapters, and the runtime engine.

Figure 7:
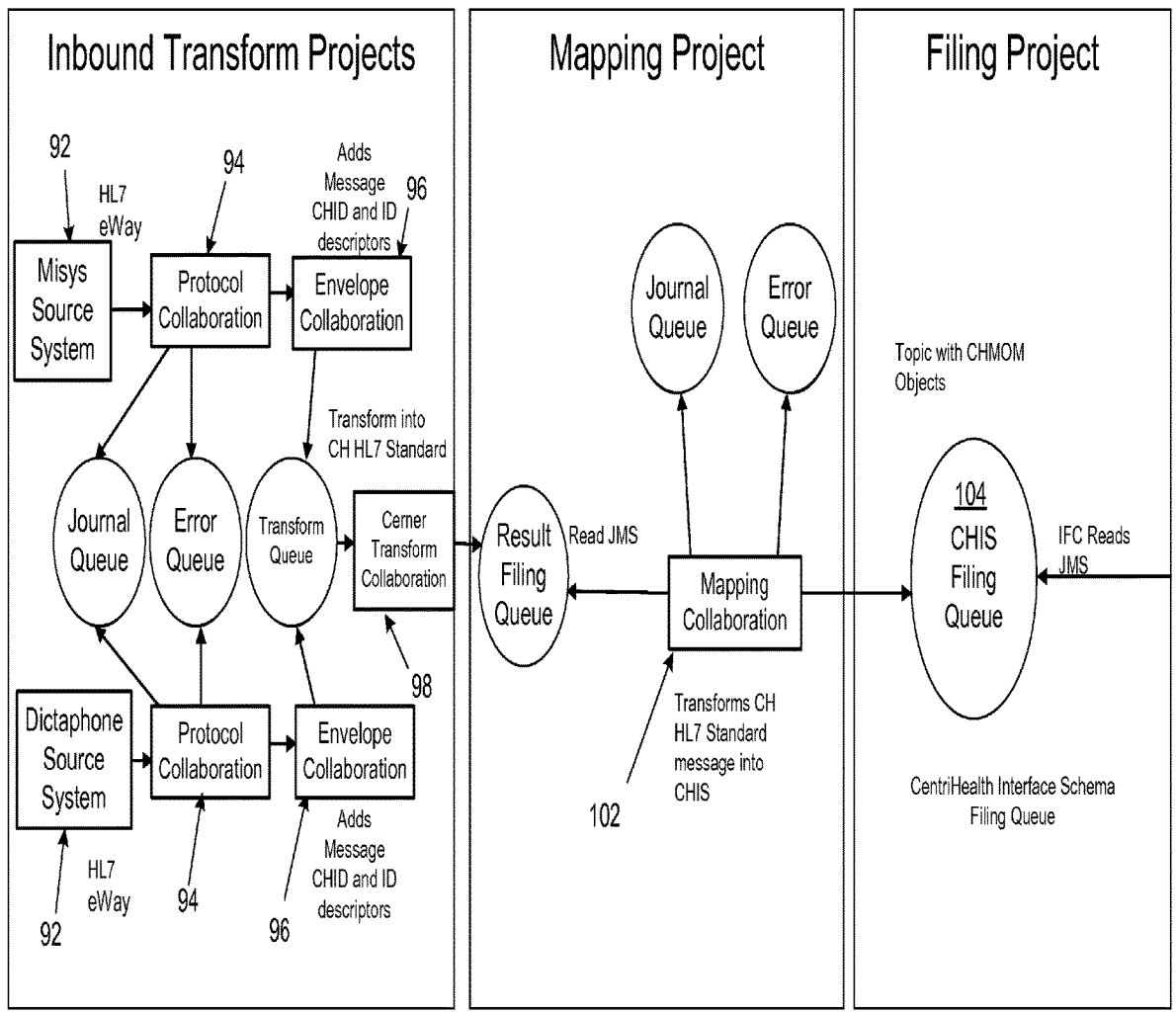
FIG. 7 is a message processing map in accordance with one embodiment of the present invention.
Figure 8:
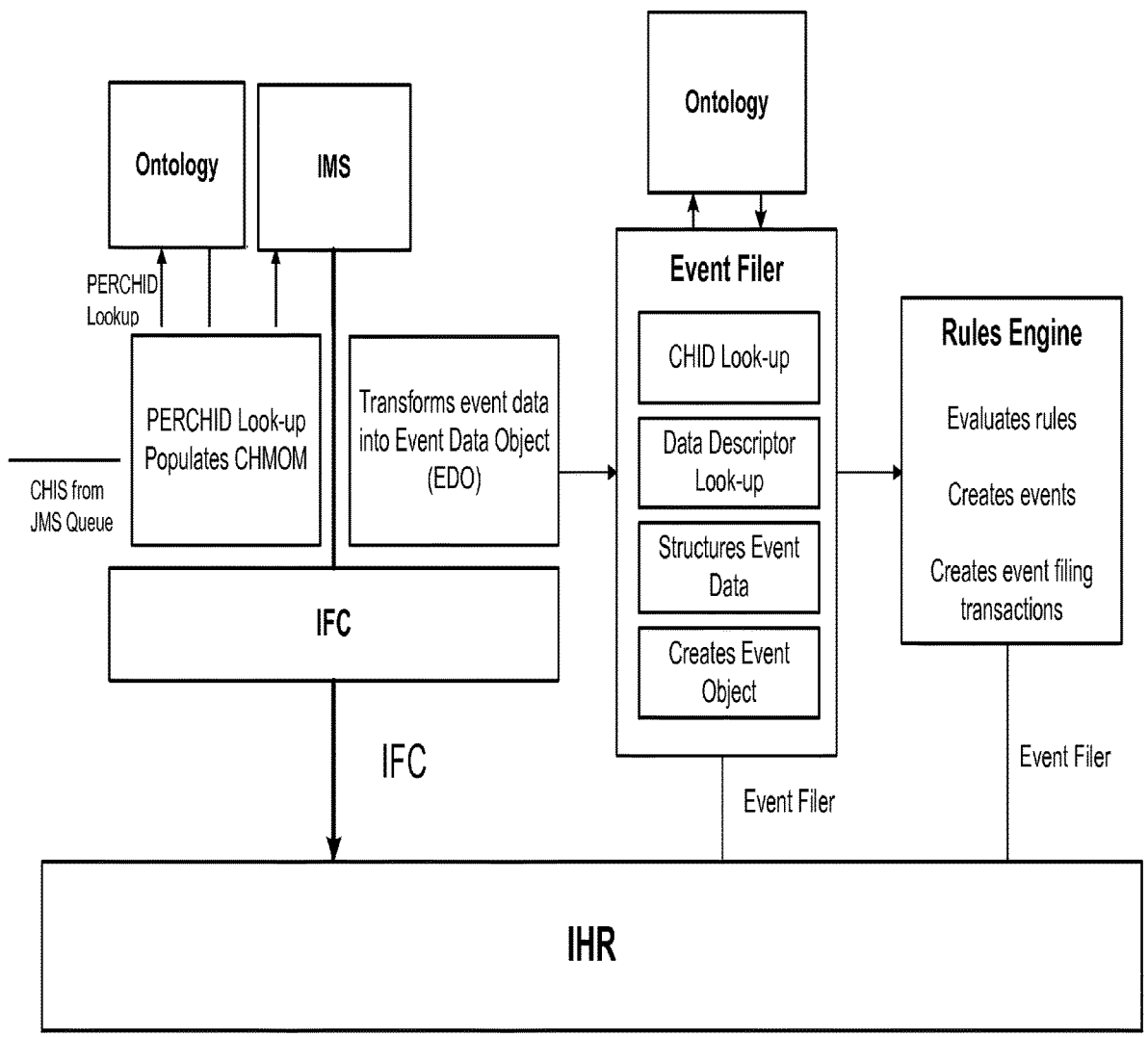
FIG. 8 is a diagram showing interface service processing in accordance with another exemplary embodiment of the present invention.
Figure 20:
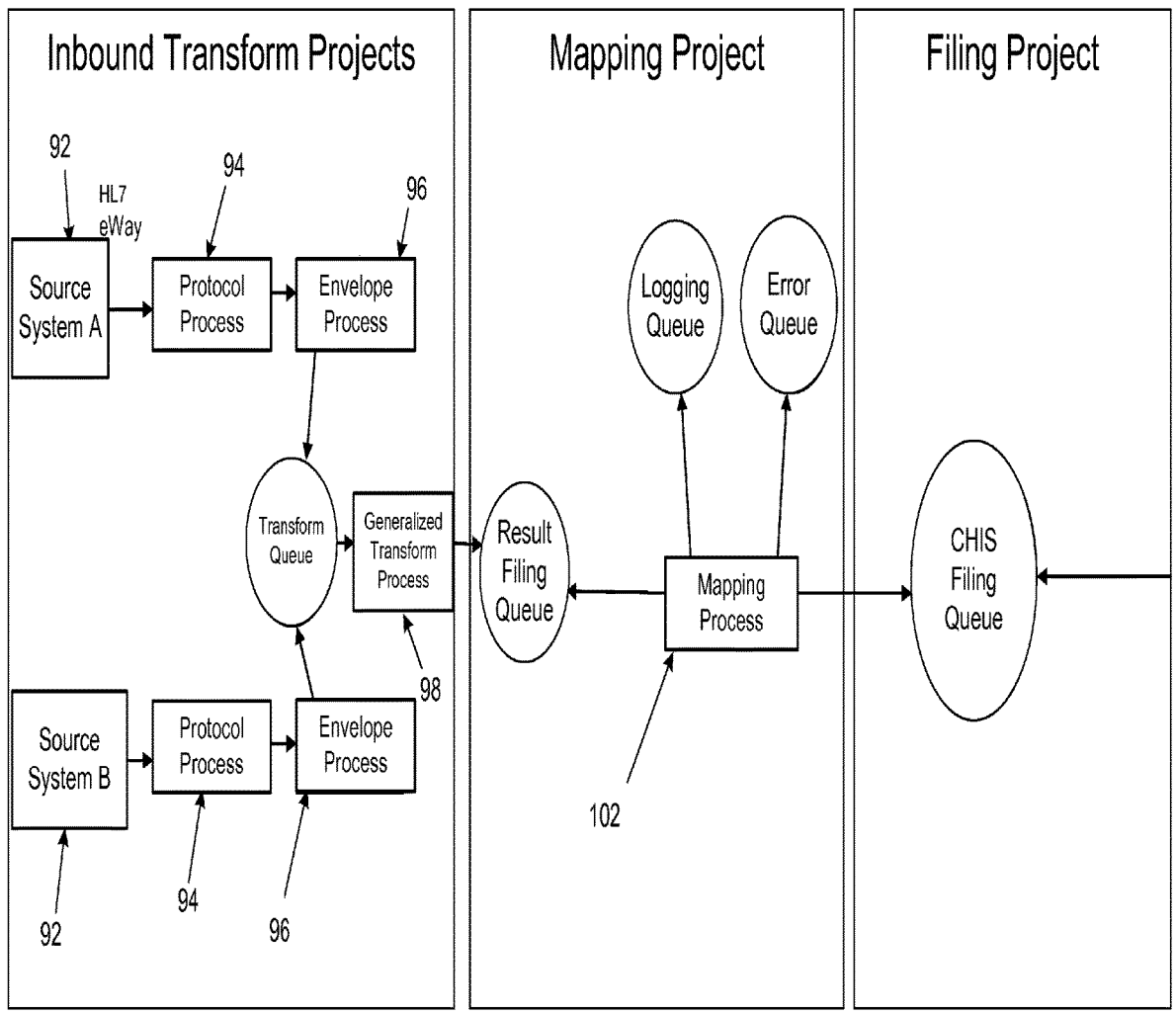
FIG. 20 is a message processing map in accordance with one embodiment of the present invention.

FIGS. 7 and 20 shows the message processing map for an exemplary embodiment of the present invention. Two examples of source systems are shown: in FIG. 20, these are a Source system A 91 and a Source system B 92. The data undergoes protocol 94 and envelope 96 processes, and undergoes transform processing 98. The data is mapped 102 and submitted to the interface schema filing queue 104. Additional interface internal processing is shown in FIG. 8.

In another exemplary embodiment, the present invention comprises a Single Best Record (SBR). The SBR comprises a healthcare object containing the "very best" composite information known about a healthcare event, test, or the like. In current healthcare electronic records systems and operations, the systems rely on individuals to examine large amounts of information about an individual patient (many instances of this information, in fact, referring to the same event), and then manually determine which portions of which instances should be considered relevant. For example, a mammogram might first be reported via an appointment request, then subsequently by a visit summary when the patient checks in, then a report of the exam several days later, then a claim submissions for payment, then the payment for the exam. In prior art systems, these would be separate records and it would be up to the user to glean the important information from each, even though they all actually refer to the same actual event. The processes of the SBR of the present invention allow all of these records and data sources to be evaluated and properly combined into a single SBR object, containing the "very best" information known about the mammogram from all sources. In short, fragmented partial information about real world health events, received as information events, is 10 reconstituted into a coherent account of those real world events. The SBR object may then be instantiated into the IHR system. Data received at a later time (whether a month, year, or even later) can be subjected to the SBR process upon receipt, contextualized into the appropriate SBR object, and seamlessly made part of the individual's health record.

The SBR process operates by taking each data input as an "information event." Information events do not necessarily have a one-to-one correspondence with real life events. Information events represent the way information about an individual can be received from any source at any time. From each information event, specific subsets of key health data are subjected to the SBR process (i.e., evaluated and combined into the SBR object) to create or update the IHR system's knowledge about a particular individual. This process could include, for example, updating a service, a date, a condition, a product, a test, or the like. Each information event may be compared to existing objects in the IHR system to determine if the information event is describing a new health event or is providing additional information on a known health event and if so whether it is an improvement on what is already known. The SBR process thereby uniquely combines what is learned from external sources with what is already known about that health event or concept to deliver composite information where previously there had only been fragmented data.

In some embodiments, a person SBR may be created, comprising a composite set of the best demographic data the IHR system knows about an entity. Demographic data from each person data object (i.e., each event) is used to update the person SBR.

In one embodiment, the IHR system is dependent on the ability to accurately identify or create an entity, and link data correctly. Identity management services (IMS) 62 handle these functions. In an exemplary embodiment, two types of entities are of particular importance: persons (including, but not limited to, patients, members, consumers, clinicians, and individuals), and organizations (including, but not limited to, employers, payors, and providers, such as hospitals, reference labs, imaging centers, or nursing homes). IMS functions include creation, matching, merging, and unmerging for each type of entity.

One goal of identity matching is to have the disparate data about an entity from multiple source be placed in or inserted into a single record (e.g., the SBR). The persons and/or organizations within a message or input data are matched to the persons and organizations known to the IHR system (or creates a new record for the entity if none previously exists). The identity matching process returns a CHID that has been assigned to the entity. Alternatively, criteria matching can be used to effect a match. Criteria may comprise demographic information (e.g., name, birth date, gender, address, telephone number, email address, mother's maiden name), identifiers (e.g., medical record number, social security number, member number, provider ID, driver's license ID), or relationship information (e.g., family data, service provider relationship). Probablilistic matching may also be used.

For criteria based matching, in one exemplary embodiment, a library or table of matching criteria rules may be used. Rules may exist for person matching, or organization matching. Each rule may comprise one or more criteria which must be met to achieve a successful match. Rules may be electronic system specific. As best practices are established, they may be applied to other electronic systems.

If the system determines that no match exists, then the system may create a new entity record.

In one exemplary embodiment, all demographic source data is treated like any other data object; any demographic source data received in a message, form or web service input will create an event. This permits the system to display the demographic date in the relevant event, and be able to "rematch" the person and/or re-SBR as needed.

Figure 9:
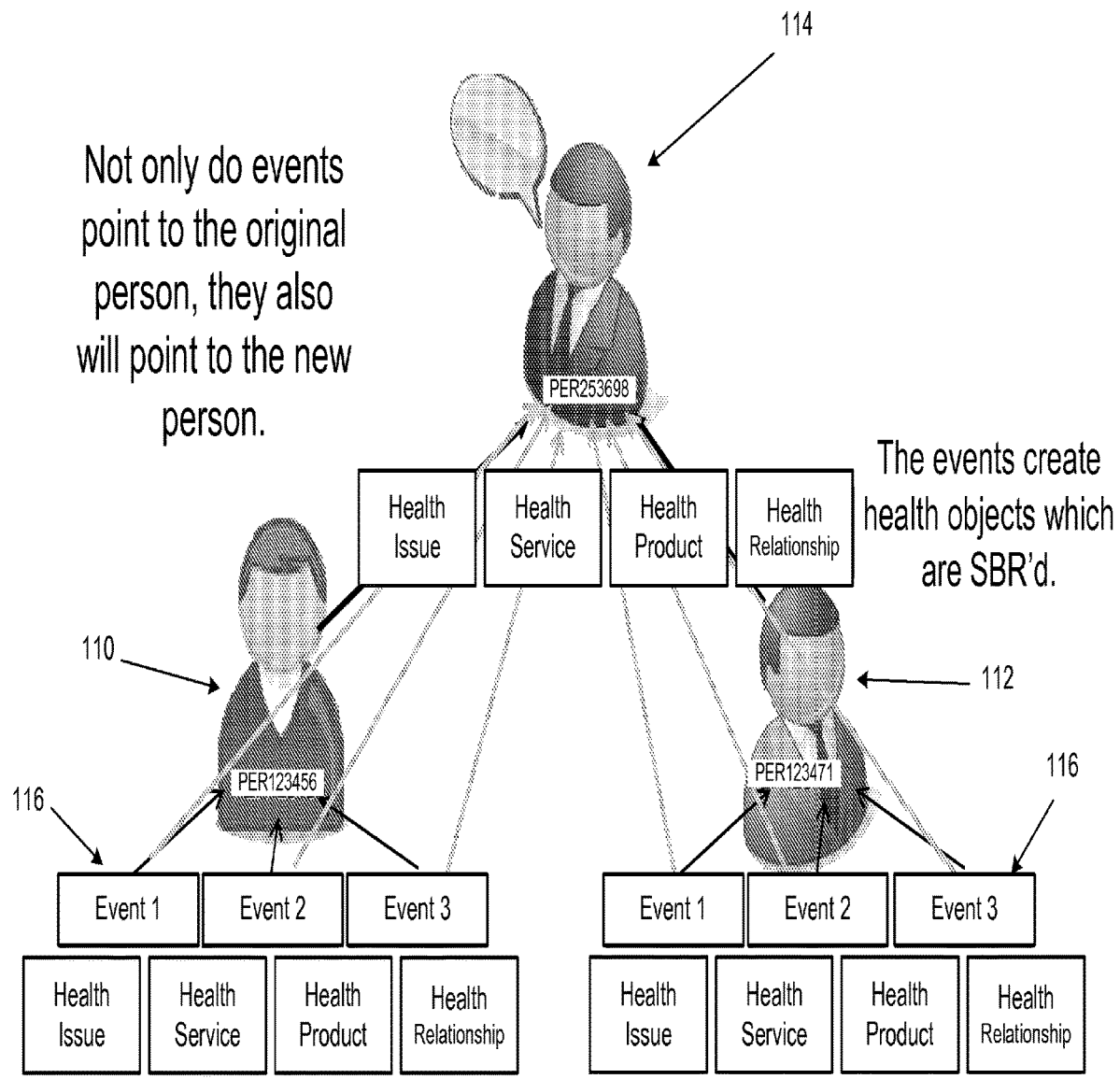
FIG. 9 is a diagram showing merger of entities in accordance with an exemplary embodiment of the present invention.

In another embodiment, when two entities 110, 112 are recognized by the system to be the same entity, they are effectively merged by creating a third entity 114, as shown in FIG. 9. The data and events from the two entities are merged. Not only do events 116 point to the original entity, but they also point to the new entity. New events need to be attached properly: new data is attached to the most specific (lowest level) entity, as well as higher level entities. Any new data generated directly by or on the merged entity will be attached to that entity. Merged entities may themselves be merged.

Conversely, entities may be unmerged (i.e., linked entities are separated). Audit histories may be created for each entity involved in the unmerged, and formerly merged entities can be accessed through the audit history. In the unmerging process, any events on the merged entity must be manually assigned to the appropriate lower level entity.

In yet another exemplary embodiment, the present system comprises a unique health ontology to overcome limitations of the prior art in representing knowledge and information. A uniform and unifying way of dealing with health information is highly desirable. Most prior art systems contain some type of coding scheme, internal or external. Some of the more popular schemes include the Standardized Nomenclature of Medicine (SNOMED), and ICD-9 or ICD-10 (the International Classification of Disease, including the clinical modification variations). While these coding schemes have long been proposed as needed for health IT systems, and have been adopted and used by many systems, they have been used primarily in retrospective studies, and have not had the desired impact on real-time health delivery.

Ontology is a body of formally represented knowledge comprising a set of concepts, their definitions, and their relationship for a specific domain (in this case, health and healthcare). The ontology of the present system is far more than a coding scheme; it not only is a way of representing every concept in health care, but also a way or representing how such concepts interrelate for the purpose of supporting the health care of individuals and the ways in which such concepts can be referenced and invoked.

In one exemplary embodiment, the system's ontology services function by reducing each piece of received information to a centrified health identifier (CHID). Each CHID has both relationship and attribute information, allowing it to know far more about the meaning of that isolated piece of information in relation to the individual than just the information received. For example, a C-section is not just a surgical procedure.

There are a number of "knowledge concepts" that can be inferred by virtue of the fact that a patient has had a C-section. The various health care coding schemes that are available with regard to any particular patient may relate not only to the C-section but, perhaps, to other findings related to a C-section. These interrelationships are represented in the ontology, so that the universe of issues and findings to be associated with such a patient becomes part of the inherent knowledge used and conveyed by the subject invention. For instance, if it is known that an individual has a C-section, the ontology also informs the system that the individual is a female, has been pregnant (gravida >0), and has had a non-vaginal delivery of a fetus or a child, among other things. As another example, the structure and content of the ontology means that an elevated Hemoglobin A 1C informs not only that the person has diabetes, but also the inheritance of an entire class of characteristics of people that have diabetes. The ontology is "full of attributes that identify characteristics of a given concept, including but not limited to how it is displayed, where it is displayed, and what privacy and confidentiality treatments apply. Data may be stored both as original source vocabulary code, and as IHR concept code (e.g., CHID).

In one exemplary embodiment, the ontology of the present invention comprises over 1,500,000 source vocabulary terms, referencing over 300,000 distinct concepts represented as CHIDs. There are a large plurality of linkages among the CHIDs and the concepts that can become more mature and meaningful as additional use cases are examined and incorporated into the system. Concepts can be mapped bidirectionally to and from various source vocabularies. This representation of information allows operations not possible in the prior art. As a nonlimiting example, patients and caregivers can have the benefit of the effective application of rules-based care algorithms (such as are putatively applied by disease management companies) in real time, as opposed to the delayed, after-the-fact interventions that are usually applied by quality monitoring and disease management companies.

In another exemplary embodiment, ontology web services identify and deliver the appropriate concept from the IHR system ontology. Examples of methods used by ontology web services include getCHID (used when a foreign key is passed in order to retrieve a mapped CHID), getForeignKey (used when a CHID is passed in order to retrieve a mapped foreign concept ID), getName (used to retrieve a system controlled medical vocabulary concept term), and getForeign (used to retrieve a foreign vocabulary concept term).

In exemplary embodiments, the use of the ontology to cross all sources, uses, and users of data to provide an individual-centric view and to support the determination of the proper single best record is unique.

Figure 10:
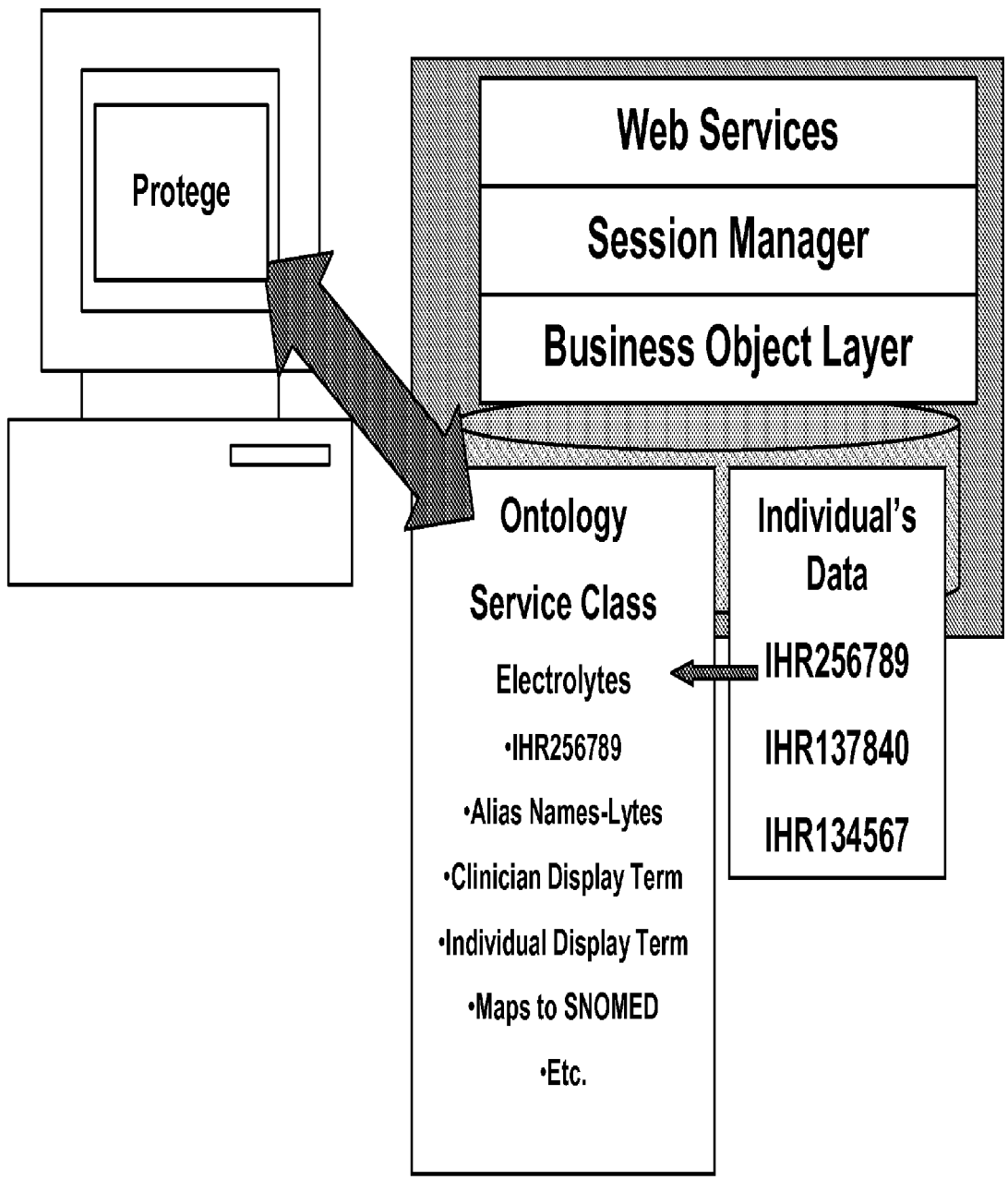
FIG. 10 is a diagram showing the relationship of the ontology tool to the IHR database in accordance with an exemplary embodiment of the present invention.
Figure 21:
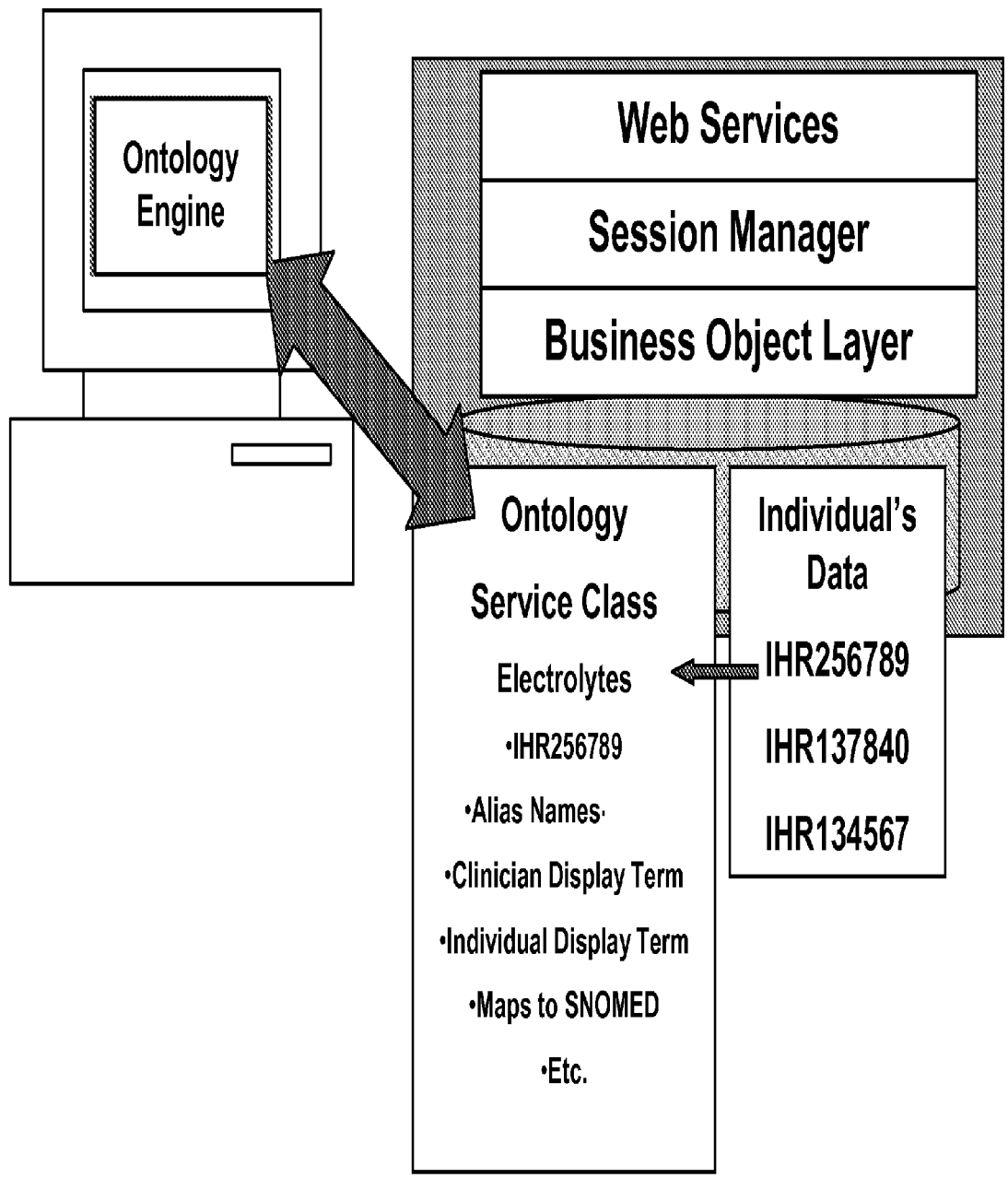
FIG. 21 is a diagram showing the relationship of the ontology tool to the IHR database in accordance with an exemplary embodiment of the present invention.
Figure 22:
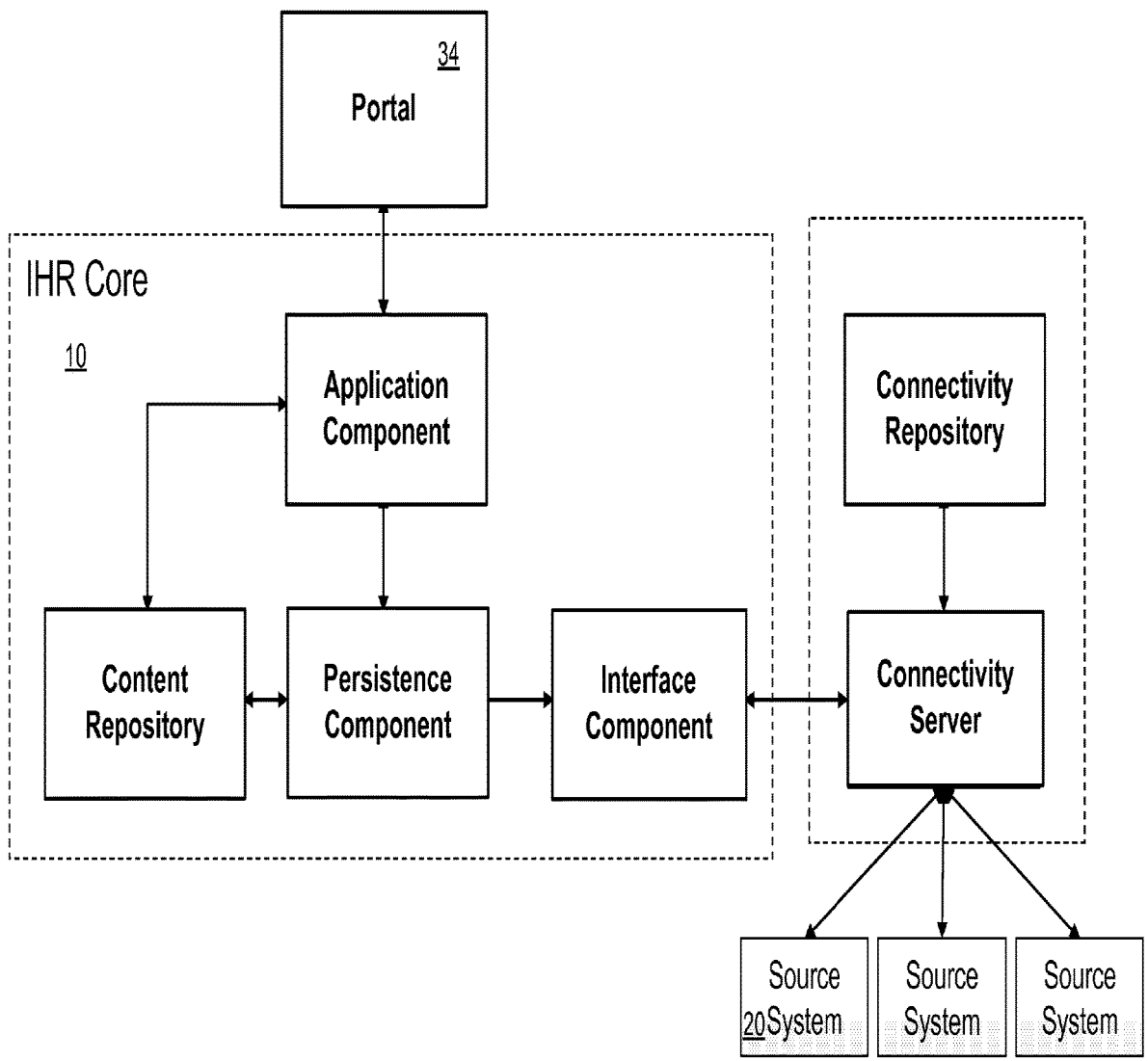
FIG. 22 is a diagram showing elements of an appliance in accordance with an exemplary embodiment of the present invention.

Another goal of the ontology is to enable data in the IHR system to "interoperate" using rules that create alerts and reminders, update the individual's health status, monitor health action progress, and similar activities. To achieve this, the data in the IHR system must be coded, have context and meaning, be linked to content, and be comparable (as seen in FIGS. 10 and 21). Benefits gained from this system are improved interoperability, increased user adoption, better clinical decision-making, reduction of medical errors, improved data mining, and the support of better outcomes analysis, among others.

Source vocabularies include a number of code systems and sets. These include, but are not limited to, the following: ANSI X.12 (standard for defining electronic data exchange of healthcare administrative transactions); ANSI HL-7 versions 2 and 3 (standards for the exchange, management and integration of electronic healthcare information); CPT (Current Procedural Terminology); HCPCS (Healthcare Common Procedure Coding System); ICD-9-CM and ICD-10 (International Classification of Diseases and Procedures); ISO (Internal Standards Organization); LOINC (Logical Observation Identifiers, Names and Codes); NACIS (Northern American Industry Classification System); NCPDP (script ePrescribing standard); NDC (National Drug 10 Codes); NUBC (National Uniform Billing Code); RxNom (nomenclature for clinical drugs); and SNOMED CT (Systematized Nomenclature of Medicine). Proprietary code sets from source systems may also be used as needed.

In one exemplary embodiment, a central ontology may be maintained and updated on a continuing basis by a service provider. When significant changes are made, the updated ontology is released. Custodians and health advocates may be able to make local extensions to their ontology.

In another exemplary embodiment, the system comprises a connectivity application module that supports the IHR system approach of taking data from any authenticated source at any time. The connectivity application module receives, understands, and processes data, information and messages regardless of the type, allowing almost any type or kind of source to provide information to the IHR system. In one exemplary embodiment, information from over 150 sourcing systems can be incorporated in a particular installation of the IHR system. The number of sourcing systems is unlimited.

In yet another embodiment of the IHR system, the presence of understandable and understood data in the system provides the opportunity to patients, caregivers, and other users to actually use the data for a wide variety of uses and applications. Such uses include, but are not limited to, quality enhancement (e.g., duplicate blocking, interaction detection and resolution, real-time adherence to disease management and other protocols, and best practices enforcement), and efficacy/efficiency optimization. Many of these uses and applications may be accomplished through a rules detection and execution environment, which may be seamless incorporated into the IHR system to provide a heretofore unavailable level of rules integration.

The IHR rules environment follows the objects created for the system using fully ontologized data. Each time an object is created or modified, all applicable rules are evaluated to see if particular criteria are met. The process includes, but is not limited to, the updating of all status indicators, and the sourcing and scheduling of rules involving time-dependent criteria (e.g., one mammogram per year for females over 40). Accordingly, in one exemplary embodiment, with every data creation or modification event, and with every tick of the clock, the potential exists for rules to execute. Rules also can trigger other rules, supporting the complexity of the health delivery system as it actually works.

An individual's health status indicators thus may be as up-to-date as the data received into the IHR system. Whenever new data is added to an individual's IHR (or data is modified), rules are evaluated. A rule scheduler may also be used and an object may schedule itself at specific frequencies. The scheduler executes rules evaluation for time-dependent criteria. This may include age-dependent rules. Kick-off notifications may be given at appropriate times prior to health action due dates as well.

In general terms, the IHR system may use rules to categorize individuals and users, update and notify users of the individual's health status, generate health maintenance actions, process action plans, create data from other data, perform data entry business logic, protective monitoring, data entry edit checks, select appropriate CHIDs, the flow of applications, support subscription-publication services, and present personalized content. Nonlimiting examples of rule applications also may include the following: create health issue objects; create health services objects; update status; update an action plan; trigger a secure message; trigger a reminder; invoke a content display; list an entry; send a message to an external system; send a fax; supplement a list; and add to the health calendar.

In one exemplary embodiment, business rules are managed independently of application code changes. Non-programmers may be provided with the ability to create and change rule. This ability may be provided through add-on decision table support. Multiple rule types may be supported, and an audit trail of rule changes may be maintained. Decision tables may be used to represent conditional logic. Spreadsheet programs may be used to set up rules. Rule creators can define parameters while scripts that map the rule data to the underlying object model are hidden.

When a rule is true, an action is triggered. Actions may include, but are not limited to, the following: creation of health issue objects; creation of health service objects; update status indicator; update action plan; secure a message; reminders; content display; list entry; health calendar entry; send a message to an external system; or send a fax.

Another exemplary embodiment of the present invention comprises a repurposing object program (ROP). The ROP overcomes a fundamental limitation of many prior systems where the early delineation of what each data item is for, and why, forever pigeonholes each data element received. In the IHR system, the data received by the system can be used for a variety of purposes, many originally contemplated when the system was assembled. The ROP, in conjunction with the above features, results in a system allowing repurposing of the data.

The combination of the above processes and components results in a process known as centrification. The centrification process takes fragmented, poorly formatted, and often incomprehensible health care data, and turns it into useful, individual-centric health care information.

In one exemplary embodiment, the conceptualization, design, development, and implementation processes that have resulted in the ontology with specific reference to health care, have been generalized and applied throughout the entire system. Some or all of the application constructs (such as, but not limited to, the display and rendering models, labels, input fields, and content managers) are codified, allowing them to be controlled non-programmatically.

In yet another embodiment, the IHR system uses a metadata content control model which allows content from a plurality of streams and sources to be matched, displayed, and linked with appropriate keys provided through the ontology or other IHR system services. This provides a level of personalization with regard to content display to both individual and professional users that is not present in the prior art.

Figure 11:
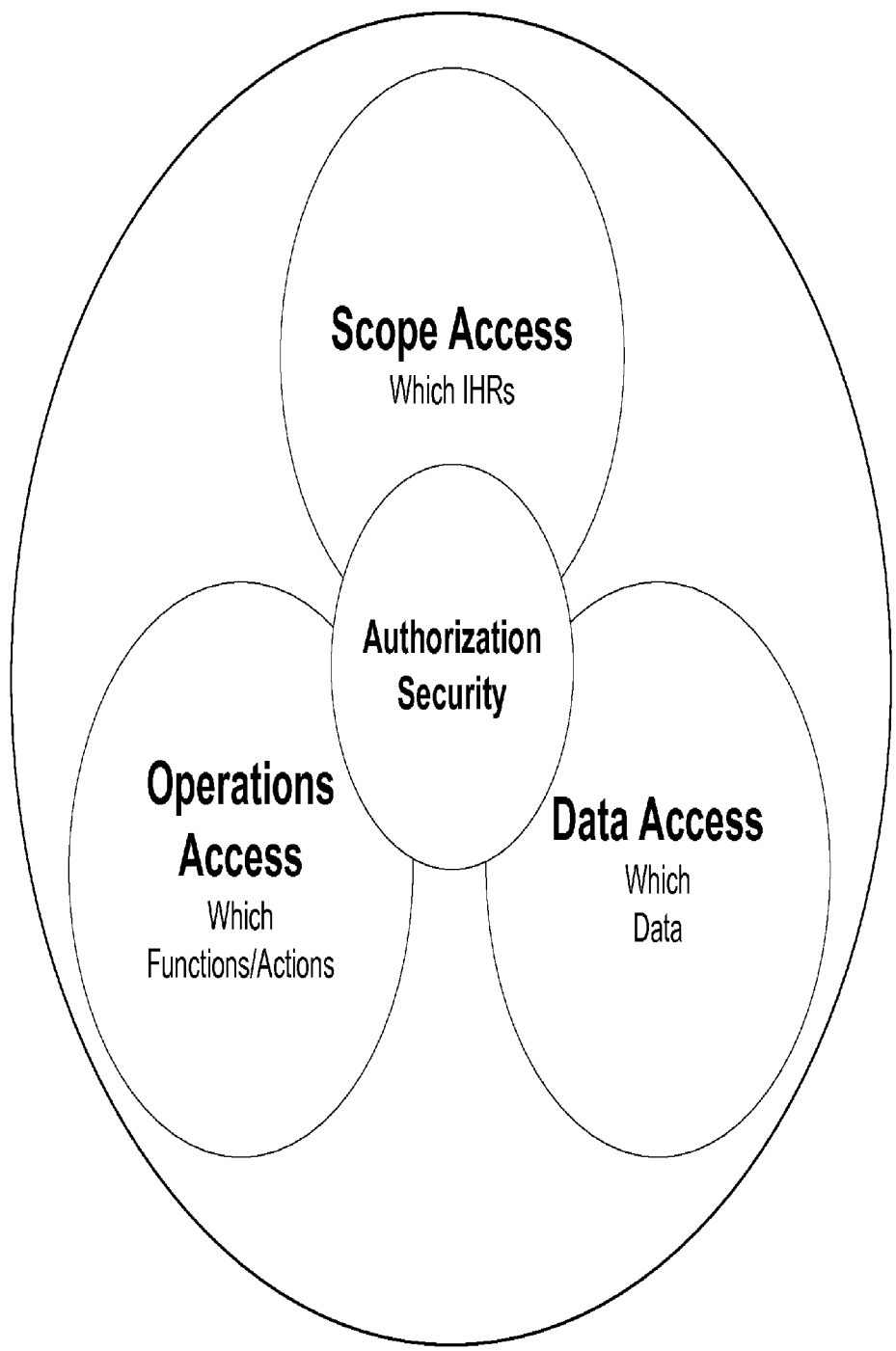
FIG. 11 is a diagram showing authorization rights components in accordance with an exemplary embodiment of the present invention.

In another exemplary embodiment, the IHR system comprises security custodial services. Prior art security models are premised on having a known, predictable pattern of system use, user types, and data—all installed in an environment where certain limitations can be imposed by and on the data custodian. In addition, security models in the prior art are too structured and rigid to work in an environment where many classes of users use the same record for different purposes. In contrast, the IHR system recognizes that neither the amount of information to be secured nor the level of detail can be presumed in advance. The IHR system is designed to deal with a variety of users, including, but not limited to, the following: patients; consumers; users who delegate their security to a custodian; and to users who come and go on the system with a need for auditing oversight but not for direct custodial intervention. The IHR system is fully adaptive: in each case, services evaluate what data to secure, what is known about the entities with potential access to this data, and what the outcome of the combination should be. As shown in FIG. 11, the authorization rights components may comprise scope access, operations access, and data access elements.

In an exemplary embodiment, data access depends on the class of data, which can include protected health information, sensitive health information, and authored protected health information. Protected health information (PHI) is used herein to refer to information that relates to the past, present, or future physical or mental health or condition of an individual, the provision of health care to an individual, or the past, present or future payment for the provision of health care to an individual, and that identifies or could reasonably be used to identify the individual. Sensitive PHI is used herein to refer to PHI that pertains to (i) an individual's HIV status or treatment of an individual for an HIV-related illness or AIDS, (ii) an individual's substance abuse condition or the treatment of an individual for a substance abuse disorder, or (iii) an individual's mental health condition or treatment of an individual for mental illness. Authored PHI is information authored by a particular user as an event initiator or performer. In various exemplary embodiment, the treatment of individual health data complies with all regulations and laws, including but not limited to HIPAA.

In one exemplary embodiment, the IHR custodial services comprise a security architecture based on relationships that the IHR system knows and/or can infer between and among entities. What an IHR system user can access, called "scope," is dynamically redefined as more and more data is known about an individual. As data is received from messages and other sources, including but not limited to direct data entry or network or Web service interactions with source systems, the relationships between entities are gleaned, codified, and used to maintain the best known information about that relationship. So, all of the relevant connections are recorded and summarized into the SBR of each relationship.

When a user accesses a IHR system access point, such as a health portlet, the scope defined in the user's set of rights is evaluated. When the user performs an operation, only the data and information of the health records that match the relationship parameters are returned.

Figure 12:
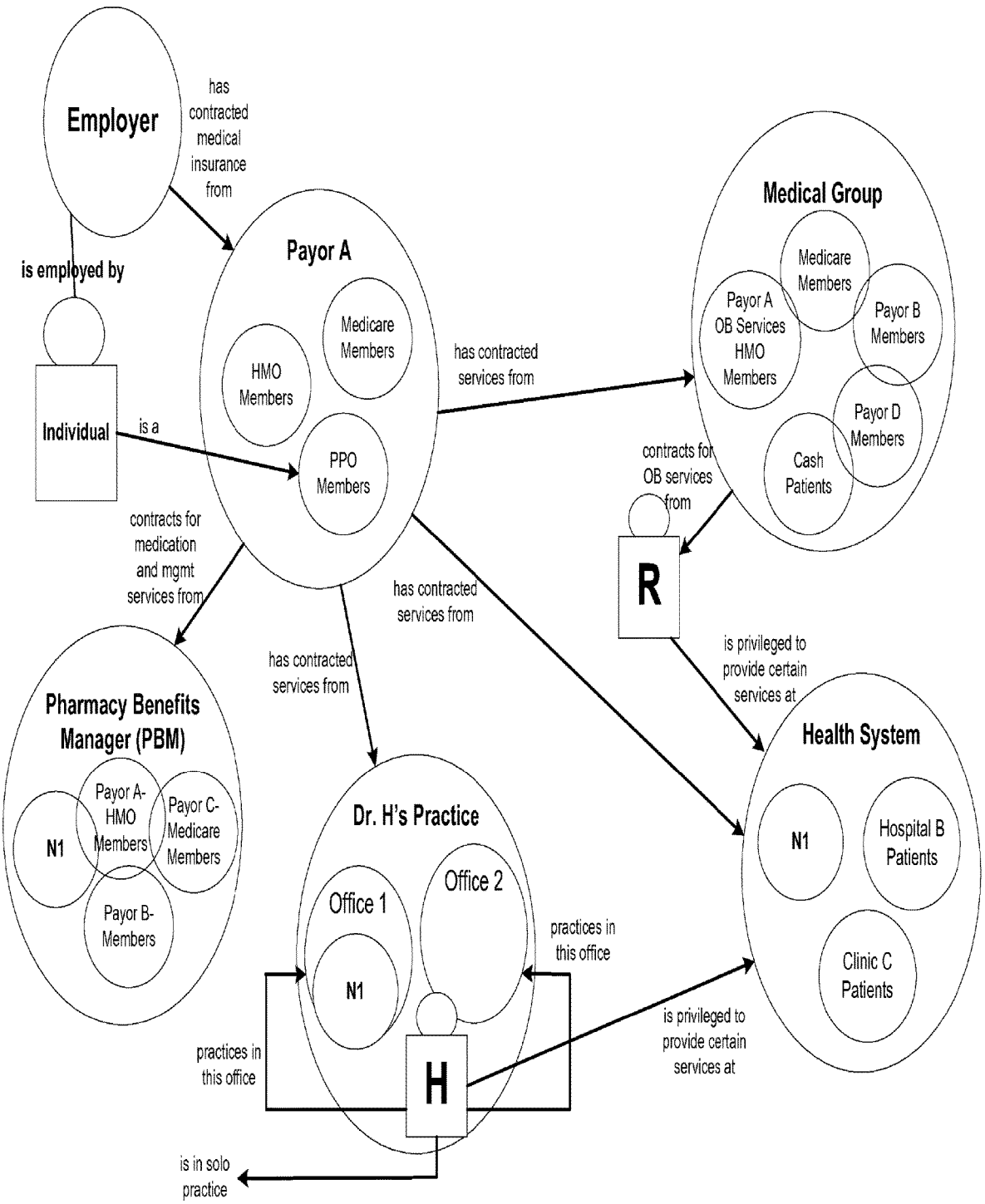
FIG. 12 is a schematic diagram of an example of individual's care relationships.

Scope access is based on the user's relationship to the individual. An example of an individual's care relationships is shown in FIG. 12. Only users with a "legitimate relationship" with the individual will have access to records concerning the individual. In one exemplary embodiment, a legitimate relationship in the IHR system is a health relationship.

The security architecture comprises a number of other unique custodial services. Prior art systems often overlook that in health systems, security should be performed at the data element level, not the record level, and thus either restrict complete access to a patient's data, or restrict access to a complete class of patient information (e.g., insurance information). What is needed is the ability to restrict to any element (e.g., medical concept) of patient information. The IHR security architecture is able to restrict around particular concepts or CHIDs, or the values of a field or data element, or some combination thereof. This permits the system to restrict access or the display of any attribute of an object based on the attributes of a CHID (or other value) defined in the ontology.

Figure 13:
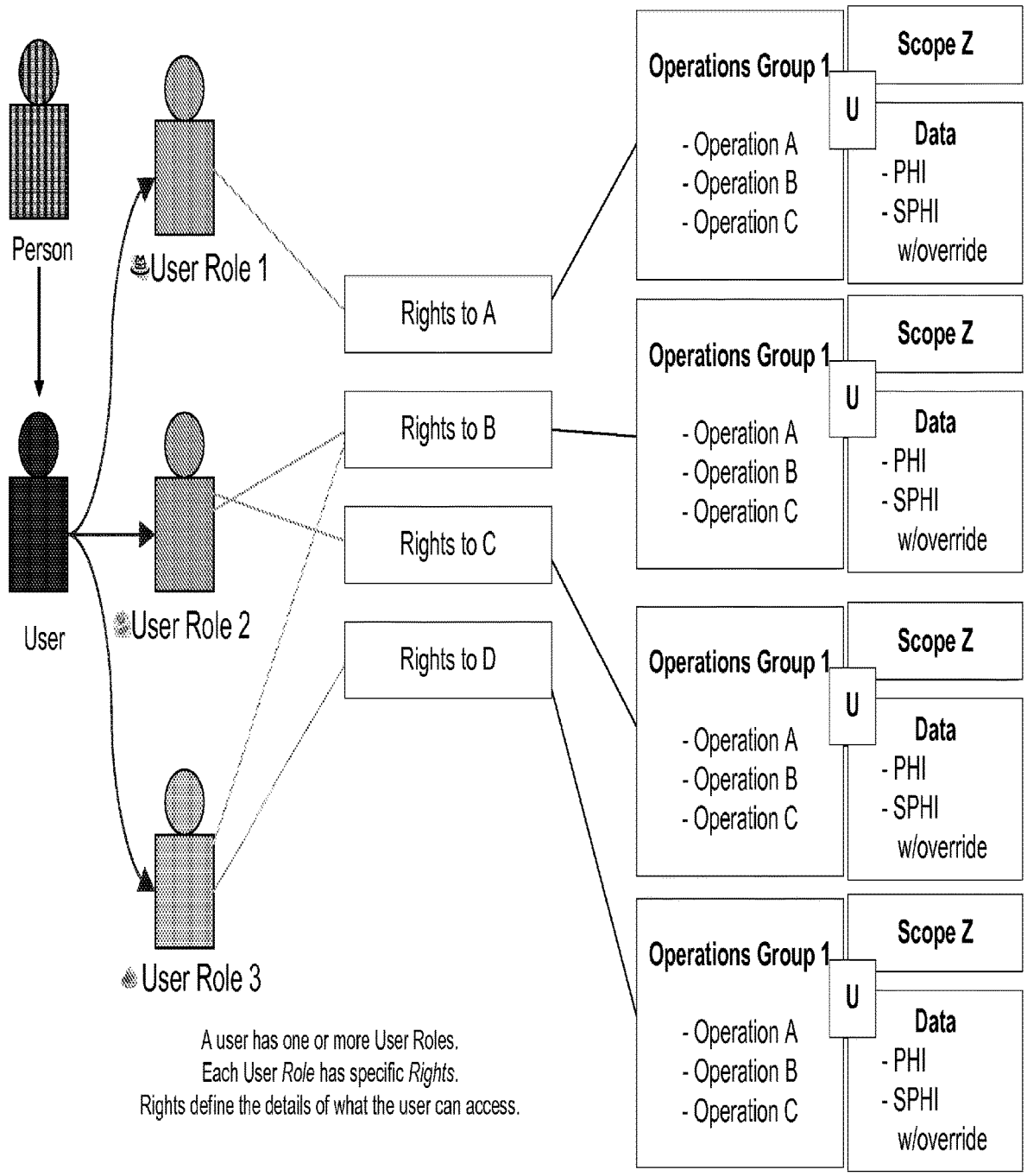
FIG. 13 shows role-based user authorization security components in accordance with an exemplary embodiment of the present invention.
Figure 14:
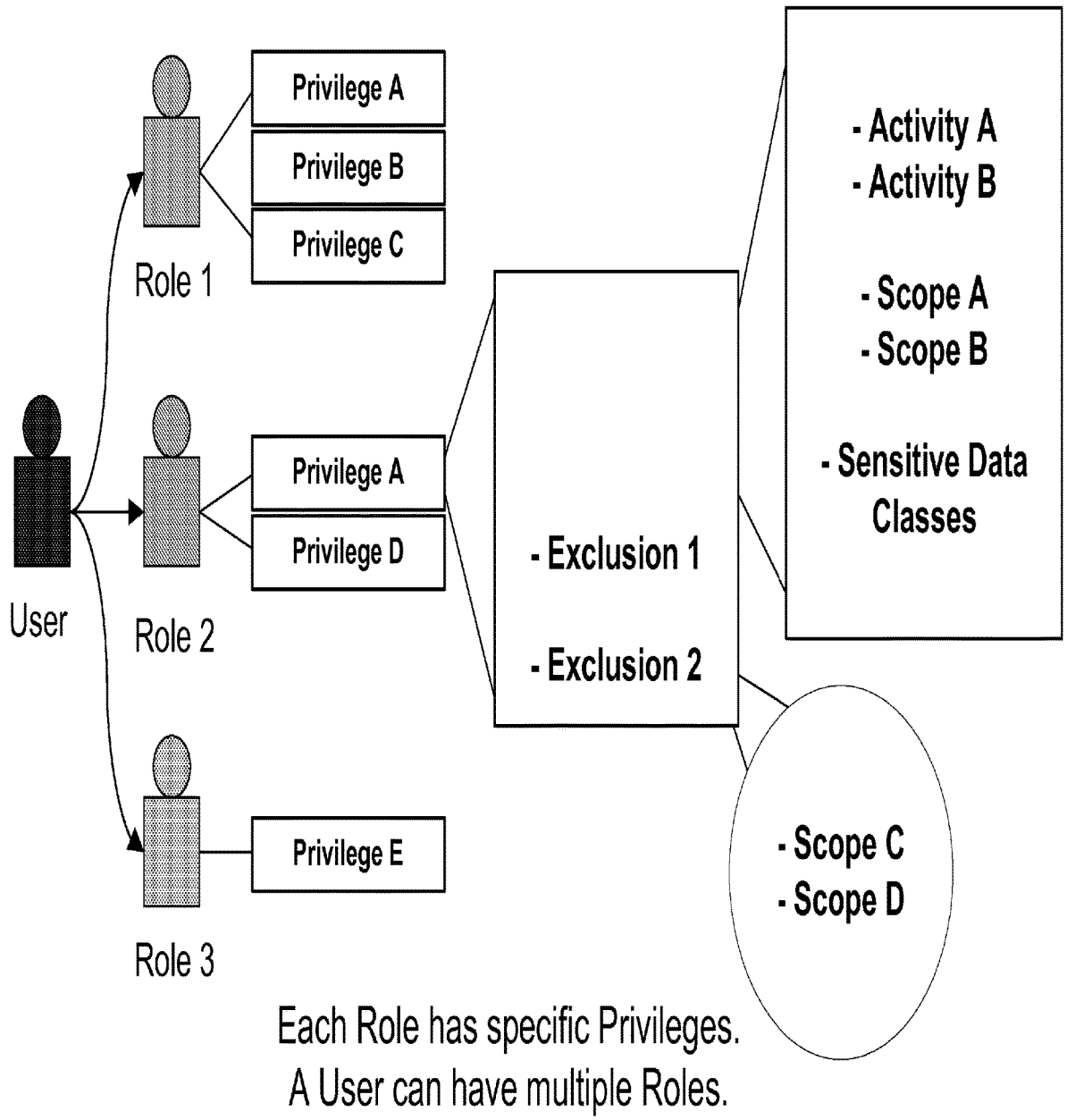
FIG. 14 shows role-based user authorization security components in accordance with an exemplary embodiment of the present invention.
Figure 15:
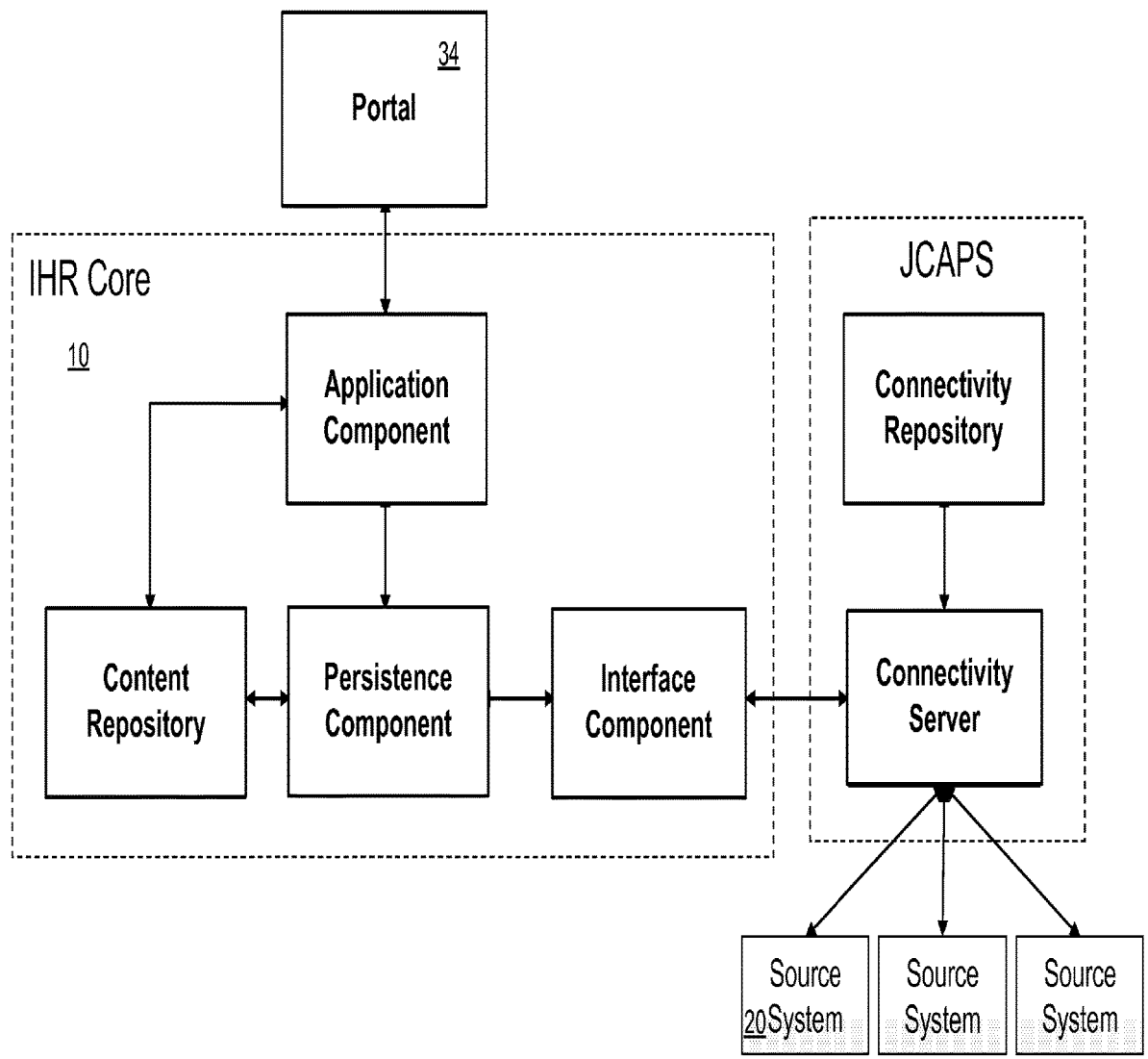
FIG. 15 is a diagram showing elements of an appliance in accordance with an exemplary embodiment of the present invention.
Figure 16:
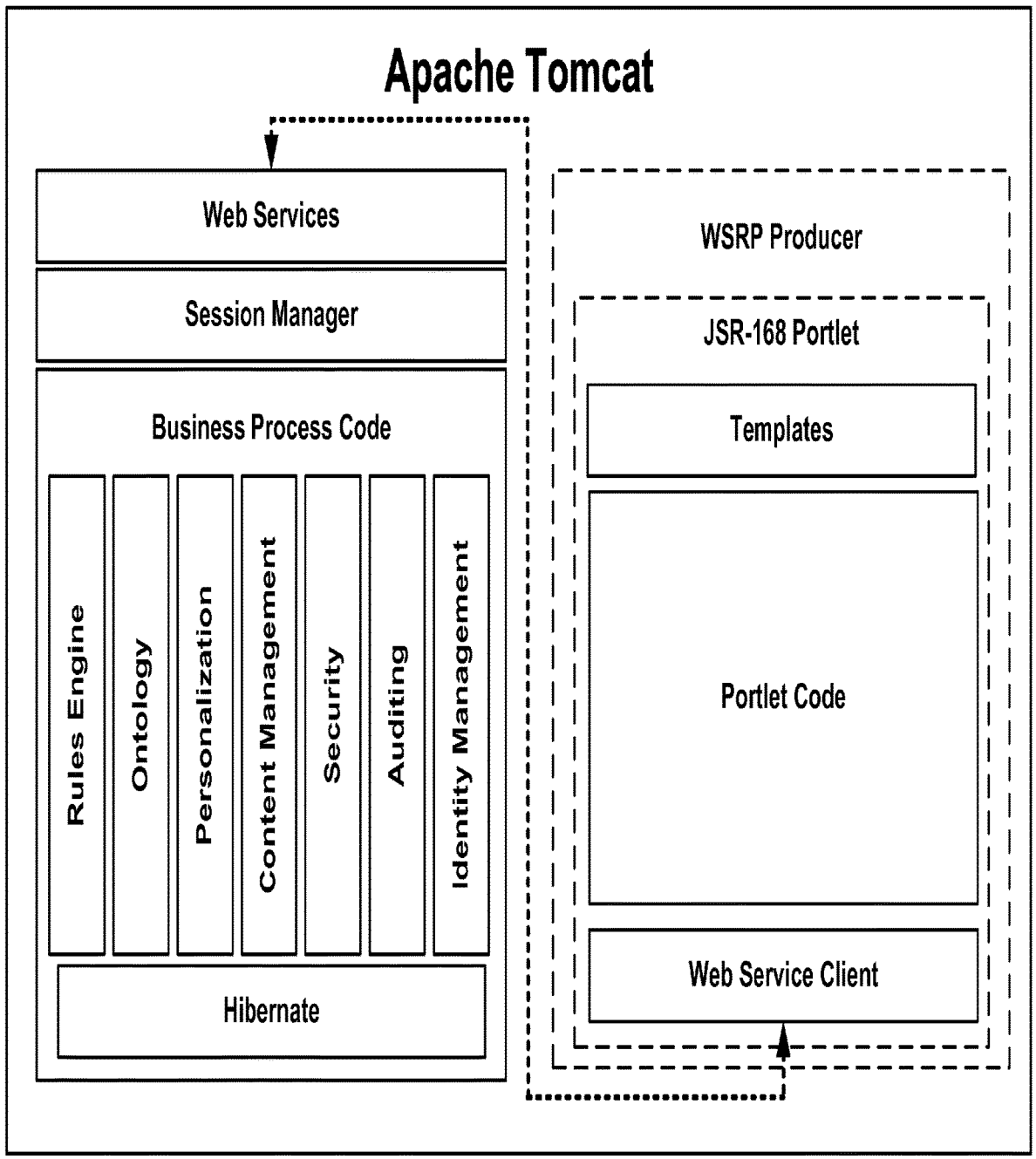
FIG. 16 is a diagram showing elements of an application server in accordance with an exemplary embodiment of the present invention.

In yet another exemplary embodiment, as seen in FIGS. 13 and 14, the IHR system comprises a multi-tiered, non-hierarchical ability to restrict access or display based on the role of a user. Role refers to the function or responsibility assumed by a person in the context of a healthcare event. Role information documents a person's association with an identified healthcare activity. Roles include, but are not limited to, provider roles (e.g., admitting, attending, billing, consulting, collaborating, interpreting, performing, referring, servicing, supervising, treating), personal roles (self, next-of-kin, emergency contact, guarantor, guardian), or organization roles (carrier, employee, employer, insured, subscriber). A user can have multiple roles 120, 121, 122, and each role can have specific rights 124, 125, 126, 127 associated with it. When the user's role or "hat" changes, the user's authorization rights change. This include scope access rights, operations access rights, and data access rights. Thus, for example, a doctor in his or her practice has different access rights than the same doctor looking at his or her own records, or the same doctor acting as a health insurance company review physician. Similarly, an individual may grant or restrict access to any or all portions of their IHR from any and all caregivers, based on a class of information (including sensitive personal health information, such as, but not limited to, psychiatric information, substance abuse information, HIV status, AIDS data, and the like). Authorized users may "break the seal" on restricted information in emergencies if that is the appropriate disposition.

The present invention provides a variety of ways and means to interact with the information in the IHR, including, but not limited to, through health portals, portlets, and web services. Thus, the invention provides a complete suite of information services and not just an end-user application. This allows the invention to support existing information systems in ways that previous "records" art could not. In one exemplary embodiment, Java standard portlets and web services are used to deliver a user interface (and user interaction) through a standard portal. A portal is a Internet based application, and serves as a starting point or gateway to other resources or applications. Portlets are user interface components or modules for a portal. Traditionally, portlets were custom applications for specific portals, although recently, portlet standards (such as JSR 168) have been defined. All interaction takes place via a communications chain extending from the portal through a portlet through the Internet service through the IHR application server. This system promotes flexibility and broad, cross-platform ubiquity in terms of accommodating users.

Connections between the IHR system and IHR portals and portlets may be encrypted. In one exemplary embodiment, a standard Internet Web browser is used to access the portal and portlets, and the connections are 128-bit SSL-encrypted connections. In addition, the support connection to all custodial sites will be via a VPN using encryption and other security mechanisms to ensure that only authorized users can access the network, and that data cannot be intercepted.

Administrative services include the backing up of various components of the system, including but not limited to database files and journal queues. Backup may be performed in stages, with frequent backups to intermediate storage, and less frequent backups to long-term storage. Disaster recovery operations and fail-over database servers also may be used for data and system security and continued operations.

In an exemplary embodiment, the IHR system is bundled into a prepackaged, self-contained package or "appliance," as shown in FIGS. 3, 15, 17 and 22. The IHR appliance is designed to "plug and play" in existing health care information technology systems and networks, with minimal effort and intervention. The appliance may be installed behind a network firewall. Information is obtained from all available source systems and dynamically constructed into the IHR. This appliance model for an application level solution at this level is new, and provides the ability to deliver any number of appliances and have them provide the IHR functions with minimal user intervention. In addition, this model permits appliances to be added to any node as necessary to deal with increases in volume without major re-architecting of the solution or the node. This allows rapid distribution and redeployment of IHR systems.

The IHR system thus allows individuals to understand and participate in their health care, and enables caregivers and consumers to collaborate and interact using the same record in different ways. It embraces the emerging roles of custodian and health care advocate, and assists health care stakeholders, including but not limited to health systems, health plans, IPAs, RHIOs, employers, providers, and individuals, to meet the requirements and needs for health care systems going forward into the future. In one exemplary embodiment, the present invention does not replace existing information systems and infrastructure; instead, it provides a standards-based, service-oriented infrastructure that rapidly and easily provides health-related information and components that work with such existing systems.

Operations available to users in various exemplary embodiments include, but are not limited to, identifying individuals, viewing an event list, filtering events, detailing events, editing events, printing events, viewing event details, managing users (e.g., adding users, editing users, editing user fields, deactivating users, identifying users), identifying individuals, and manipulating health issues (e.g., filtering, viewing list, viewing detail, adding, editing, and printing health issues).

Thus, it should be understood that the embodiments and examples have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

We claim:

1. A system comprising one or more processors and one or more memory storage areas, the one or more memory storage areas storing computer-readable program code portions, the computer-readable program code portions configured to, when executed by the one or more processors, cause the system to at least:

receive health care information originating from one or more health care information sources, wherein at least a portion of the health care information comprises electronic data records in at least one of different formats or incompatible formats; and create or modify a health care object based at least in part on the health care information, wherein (a) the health care object comprises an object-oriented software object subject to an object hierarchy, (b) the health care object is associated with an individual-centric health information model, (c) the individual-centric health information model comprises a health care ontology, (d) the health care ontology comprises (i) a set of health care concepts with respect to a health care domain, (ii) a definition for each health care concept of the set of health care concepts with respect to the health care domain, and (iii) a relationship for each health care concept of the set of health care concepts with respect to the health care domain, and (e) the health care object comprises the best composite information about a health care condition, a health care service, a health care result, a health care product, a health care test, a health care relationship, or a health care event for an individual, wherein creating or modifying the health care object comprises:
automatically validating the health care information,
automatically parsing the health care information,
automatically transforming the health care information based at least in part on the health care ontology,
automatically assigning one or more ontology concept codes to the transformed information based at least in part on the health care ontology,
automatically determining whether to (a) create a new health care object, or (b) modify an existing health care object, wherein the automatic determination is based at least in part on applying a first set of rules to determine whether at least a portion of the transformed information sufficiently matches information of the existing health care object as a function of at least one person criteria or at least one entity criteria, and using, based at least in part on the automatic determination, at least a portion the transformed information to automatically (a) create the new health care object, or (b) modify the existing health care object; and after creation or modification of the health care object, providing at least a portion of the best composite information from the health care object for a user interface to display.

2. The system of claim 1, wherein the health care information comprises object-oriented data and non-object-oriented data.

3. The system of claim 1, wherein the user interface comprises a platform-independent portal.

4. The system of claim 1, wherein the user interface comprises an Internet browser.

5. The system of claim 1, wherein the system comprises a single self-contained appliance device adapted to be incorporated into an existing network or information technology system.

6. The system of claim 1, wherein the system comprises a plurality of self-contained appliance devices, each self-contained appliance device adapted to be incorporated into an existing network or information technology system.

7. The system of claim 1, wherein creating or modifying the health care object further comprises applying a second set of rules specifying time-dependent criteria for scheduling healthcare events each time the health care object is modified.

8. A computer-implemented method comprising:

receiving, by one or more processors, health care information originating from one or more health care information sources, wherein at least a portion of the health care information comprises electronic data records in at least one of different formats or incompatible formats; and creating or modifying, by the one or more processors, a health care object based at least in part on the health care information, wherein (a) the health care object comprises an object-oriented software object subject to an object hierarchy, (b) the health care object is associated with an individual-centric health information model, (c) the individual-centric health information model comprises a health care ontology, (d) the health care ontology comprises (i) a set of health care concepts with respect to a health care domain, (ii) a definition for each health care concept of the set of health care concepts with respect to the health care domain, and (iii) a relationship for each health care concept of the set of health care concepts with respect to the health care domain, and (e) the health care object comprises the best composite information about a health care condition, a health care service, a health care result, a health care product, a health care test, a health care relationship, or a health care event for an individual, wherein creating or modifying the health care object comprises:

automatically validating the health care information,
automatically parsing the health care information,
automatically transforming the health care information based at least in part on the health care ontology,
automatically assigning one or more ontology concept codes to the transformed information based at least in part on the health care ontology,
automatically determining whether to (a) create a new health care object, or (b) modify an existing health care object, wherein the automatic determination is based at least in part on applying a first set of rules to determine whether at least a portion of the transformed information sufficiently matches information of the existing health care object as a function of at least one person criteria or at least one entity criteria, and using, based at least in part on the automatic determination, at least a portion the transformed information to automatically (a) create the new health care object, or (b) modify the existing health care object; and after creation or modification of the health care object, providing, by the one or more processors, at least a portion of the best composite information from the health care object for a user interface to display.

9. The method of claim 8, wherein the health care information comprises object-oriented data and non-object-oriented data.

10. The method of claim 8, wherein the user interface comprises a platform-independent portal.

11. The method of claim 8, wherein the user interface comprises an Internet browser.

12. The method of claim 8, wherein the method is executed by a single self-contained appliance device adapted to be incorporated into an existing network or information technology system.

13. The method of claim 8, wherein the method is executed by a plurality of self-contained appliance devices, each self-contained appliance device adapted to be incorporated into an existing network or information technology system.

14. The method of claim 8, wherein creating or modifying the health care object further comprises applying a second set of rules specifying time-dependent criteria for scheduling healthcare events each time the health care object is modified.

15. A computer program product, the computer program product comprising at least one non-transitory computer-readable storage medium having computer-readable program code portions stored therein, the computer-readable program code portions configured to cause one or more processors to at least:

receive health care information originating from one or more health care information sources, wherein at least a portion of the health care information comprises electronic data records in at least one of different formats or incompatible formats; and create or modify a health care object based at least in part on the health care information, wherein (a) the health care object comprises an object-oriented software object subject to an object hierarchy, (b) the health care object is associated with an individual-centric health information model, (c) the individual-centric health information model comprises a health care ontology, (d) the health care ontology comprises (i) a set of health care concepts with respect to a health care domain, (ii) a definition for each health care concept of the set of health care concepts with respect to the health care domain, and (iii) a relationship for each health care concept of the set of health care concepts with respect to the health care domain, and (e) the health care object comprises the best composite information about a health care condition, a health care service, a health care result, a health care product, a health care test, a health care relationship, or a health care event for an individual, wherein creating or modifying the health care object comprises:

automatically validating the health care information, automatically parsing the health care information, automatically transforming the health care information based at least in part on the health care ontology, automatically assigning one or more ontology concept codes to the transformed information based at least in part on the health care ontology, automatically determining whether to (a) create a new health care object, or (b) modify an existing health care object, wherein the automatic determination is based at least in part on applying a first set of rules to determine whether at least a portion of the transformed information sufficiently matches information of the existing health care object as a function of at least one person criteria or at least one entity criteria, and using, based at least in part on the automatic determination, at least a portion the transformed information to automatically (a) create the new health care object, or (b) modify the existing health care object; and after creation or modification of the health care object, provide at least a portion of the best composite information from the health care object for a user interface to display.

16. The computer program product of claim 15, wherein the health care information comprises object-oriented data and non-object-oriented data.

17. The computer program product of claim 15, wherein the user interface comprises a platform-independent portal.

18. The computer program product of claim 15, wherein the user interface comprises an Internet browser.

19. The computer program product of claim 15, wherein the computer-readable program code portions are executed by a single self-contained appliance device adapted to be incorporated into an existing network or information technology system.

20. The computer program product of claim 15, wherein the computer-readable program code portions are executed by a plurality of self-contained appliance devices, each self-contained appliance device adapted to be incorporated into an existing network or information technology system.

21. The computer program product of claim 15, wherein creating or modifying the health care object further comprises applying a second set of rules specifying time-dependent criteria for scheduling healthcare events each time the health care object is modified.

* * * * *